US006695780B1

(12) United States Patent
Nahum et al.

(10) Patent No.: US 6,695,780 B1
(45) Date of Patent: Feb. 24, 2004

(54) METHODS, SYSTEMS, AND COMPUTER PROGRAM PRODUCTS FOR ESTIMATING FETAL WEIGHT AT BIRTH AND RISK OF MACROSOMIA

(76) Inventors: Gerard Georges Nahum, 322 Edisto Ct., Chapel Hill, NC (US) 27514; Harold Walter Karl Stanisaw, 3816 Monteview Dr., Modesto, CA (US) 95355

( * ) Notice: Subject to any disclaimer, the term of this patent is extended or adjusted under 35 U.S.C. 154(b) by 0 days.

(21) Appl. No.: 10/273,201

(22) Filed: Oct. 17, 2002

(51) Int. Cl.⁷ .................................................. A01B 8/00
(52) U.S. Cl. ........................................................ 600/437
(58) Field of Search ................................. 600/437, 443, 600/447; 128/916; 73/602; 705/2, 3

(56) References Cited

U.S. PATENT DOCUMENTS

2002/0169637 A1 * 11/2002 Akers et al. .................... 705/3
2003/0146926 A1 * 8/2003 Valdes ......................... 345/703

OTHER PUBLICATIONS

Jazayeri,A et al "Macrosomia Prediction Using Ultrasound Fetal Abdominal Circumferenceof 35 Centimeters or More", Abstract, Jrnl Obstet Gynecol. Apr. 1999; 93(4):523–526.*
Dyck, R.F. et al "Differences in High Birthweight Rates Between Northern and Southern Saskatchewan: Implications for Aboriginal Peoples" Chronic?Diseasesin Canada vol. 16, No. 3–1995.*
Wikstrom et al., "Prediction of High Birthweight from Maternal Characteristics, Symphysis Fundal Height and Ultrasound Biometry," Gynecol Obstet Invest, p. 27–33, (1993).
Nahum et al., "Ultrasonic Prediction of Term Birth Weight in Hispanic Women," The Journal of Reproductive Medicine, p. 1–10, (Sep. 30, 2002).
Nahum et al., "Validation of a Birth Weight Prediction Equation Based on Maternal Characteristics," The Journal of Reproductive Medicine, p. 1–9, (May 22, 2002).
Krystie Quynh Pham, M.D., "Accurate Prediction of Term Birth Weight in Hispanic Women," p. 1, (2002).
Gerard Nahum, MD, FACOG, FACS, "Estimation of Fetal Weight," eMedicine Journal, p. 1–36, (Jul. 27, 2001).
Gerard G. Nahum, MD, "Detecting and Managing Fetal Macrosomia," Contemporary OB/Gyn, p. 1–12, (Jun. 2000).
Gerard G. Nahum, M.D., "Fetal Macrosomia: Detection, Risks, and Management," Postgraduate Obstetrics & Gynecology, vol. 20 (No. 10), p. 1–8, (May 2000).
Nahum et al., "Accurate Prediction of Term Birth Weight from Prospectively Measurable Maternal Characteristics," The Journal of Reproductive Medicine, vol. 44 (No. 8), p. 705–712, (Aug. 1999).
Gerard G. Nahum, FACOG, FACS, "Accurate Predition of Term Fetal Macrosomia from Prospectively Measurable Maternal Characteristics," The American College of Obstetricians and Gynecologists, p. 1, (1999).
Nahum et al., "Fetal Weight Gain at Term: Linear with Minimal Dependence on Maternal Obesity," Am J Obstet Gynecol, vol. 172, (No. 5), p. 1387–1394, (May 1995).

* cited by examiner

Primary Examiner—Francis J. Jaworski
(74) Attorney, Agent, or Firm—Jenkins, Wilson & Taylor, P.A.

(57) ABSTRACT

Methods and systems for estimating fetal weight at birth and risk of macrosomia are disclosed. Information regarding maternal characteristics and ultrasound measurements are obtained for the fetus. A computer program selects the most accurate equation from a hierarchy of birth weight/risk of macrosomia estimation equations based on the available information. Program outputs include estimated birth weight, risk of macrosomia, and confidence intervals.

53 Claims, 11 Drawing Sheets

METHODS, SYSTEMS, AND COMPUTER PROGRAM PRODUCTS FOR ESTIMATING FETAL WEIGHT AT BIRTH AND RISK OF MACROSOMIA

TECHNICAL FIELD

The present invention relates to methods, systems, and computer program products for estimating fetal weight at birth and risk of macrosomia. More particularly, the present invention relates to methods, systems, and computer program products for estimating fetal weight at birth and risk of macrosomia using a hierarchy of equations based on maternal characteristics and fetal ultrasound measurements.

RELATED ART

Obstetricians have been searching for a method to successfully predict birth weight for hundreds of years. This motivation arises because fetuses with both low and high birth weights are at increased risk for newborn complications during the intrapartum and postnatal periods. The complications associated with the delivery of excessively large fetuses include prolonged labor, shoulder dystocia, brachial plexus injury, bony injuries, and intrapartum asphyxia, as well as maternal risks of birth canal and pelvic floor injuries and postpartum hemorrhage. In addition, the occurrence of cephalopelvic disproportion is more prevalent as fetal size increases, contributing to both an increased rate of operative vaginal delivery and of cesarean section for macrosomic fetuses as compared with fetuses of normal weight. Thus, there is an increase not only in the morbidity and mortality associated with the birth of macrosomic fetuses, but also a significant increase in both the direct and indirect costs associated with their birth and lifetime care.

If fetal weight could be known with reasonable certainty in advance of delivery, the timing and mode of delivery for women carrying macrosomic fetuses could be modified to improve newborn and maternal outcomes. The problem, until now, has been appropriately identifying abnormally grown fetuses in utero, so that modifications to the patient's treatment and delivery plan could be instituted in advance of labor. Because of this, there is significant clinical utility to having a readily available tool to reliably estimate fetal weight before delivery.

Several approaches to prospective birth weight prediction have been attempted. For centuries, simply "feeling" the size of a fetus through the maternal abdominal and uterine walls was the only tool that was available. The predictive accuracy of such tactile assessment of fetal size is suboptimal, with its overall accuracy ranging from ±7.5–19.8% of actual birth weight. During the past quarter century, this technique has gradually been supplanted by the method of ultrasonographic fetal biometry. The assumption underlying this change has been that fetal biometric assessments would yield superior estimates of birth weight because the multiple fetal measurements obtained via sonography are quantitative in nature and less "subjective" than the information obtained by clinical means. This assumption presupposes that the sonographic measurements of multiple linear and planar dimensions of the fetus provide sufficient parametric information to allow for accurate algorithmic reconstruction of the three-dimensional fetal volume of varying tissue density. Consistent with these beliefs, much effort has been expended to generate best-fit fetal biometric algorithms that can make birth weight predictions based on obstetrical sonographic measurements alone. As such, the ultrasonographic technique represents the newest and most technologically sophisticated method of making fetal weight estimations. Although obstetrical ultrasonography has proven to be a boon as a tool to detect fetal anomalies, position, amniotic fluid volume and placental location, standard sonographic fetal biometric modeling has been an unfortunate failure with regard to predicting fetal weight. Its predictive accuracy has ranged from ±10.7%–15.6% of actual term birth weight, and it has never approached the level of accuracy required to make the method useful for making clinical decisions regarding optimal patient management.

Accordingly, there exists a need for improved methods and systems for estimating fetal weight at birth and risk of fetal macrosomia.

DESCRIPTION OF THE INVENTION

The present invention includes improved methods and systems for estimating fetal weight at birth and risk of macrosomia. The present invention may be implemented as a computer program that obtains information from a user and automatically estimates fetal birth weight and/or risk of macrosomia based on information provided by the user. As used herein, the term "macrosomia" refers to the condition of a fetus being born with a weight at birth that is greater than a predetermined value. The predetermined value may be based on accepted medical definitions and is preferably programmable by the user. The information used to estimate fetal weight and/or risk of macrosomia includes information regarding maternal characteristics and fetal ultrasound measurements. A user is presented with a questionnaire requesting information regarding maternal characteristics and fetal ultrasound measurements. The responses are input into fetal birth weight/macrosomia risk estimation software. The software runs through a series of logical steps that calculates fetal weight and/or risk of macrosomia based on the available information. More particularly, the software selects the most accurate equation from a uniquely devised set of equations that are empirically derived using statistical methods and multiple sets of proprietary data based on available information about the mother and/or fetal ultrasound measurements. The fetal birth weight/macrosomia risk estimation software outputs one or more numbers indicative of estimated fetal birth weight, risk of macrosomia, and confidence intervals associated therewith. Because the present invention calculates fetal weight at birth and risk of macrosomia by selecting the most accurate prediction equation for the available information, increased accuracy in predicting fetal weight at birth and risk of macrosomia is achieved. In addition, because the present invention allows for the calculation of fetal weight at birth and/or risk of macrosomia up to three months before the actual date of delivery, it allows both mothers and obstetrical practitioners time and flexibility in planning the timing and mode of delivery, so as to minimize the ultimate size of fetuses that are projected to be overgrown at particular junctures of gestation, and to minimize the risks of adverse outcomes associated with the delivery process for both these fetuses that are destined to be overgrown and their mothers. As a result, fetal injuries and injuries to the mother can be reduced.

Accordingly, it is an object of the invention to provide improved methods and systems for estimating fetal birth weight.

It is yet another object of the invention to provide improved methods and systems for estimating risk of fetal macrosomia.

Some of the objects of the invention having been stated hereinabove, and which are addressed in whole or in part by the present invention, other objects will become evident as the description proceeds when taken in connection with the accompanying drawings as best described hereinbelow.

BRIEF DESCRIPTION OF THE DRAWINGS

Preferred embodiments of the invention will now be explained with reference to the accompanying drawings of which.

DETAILED DESCRIPTION OF THE INVENTION

Figure 1:
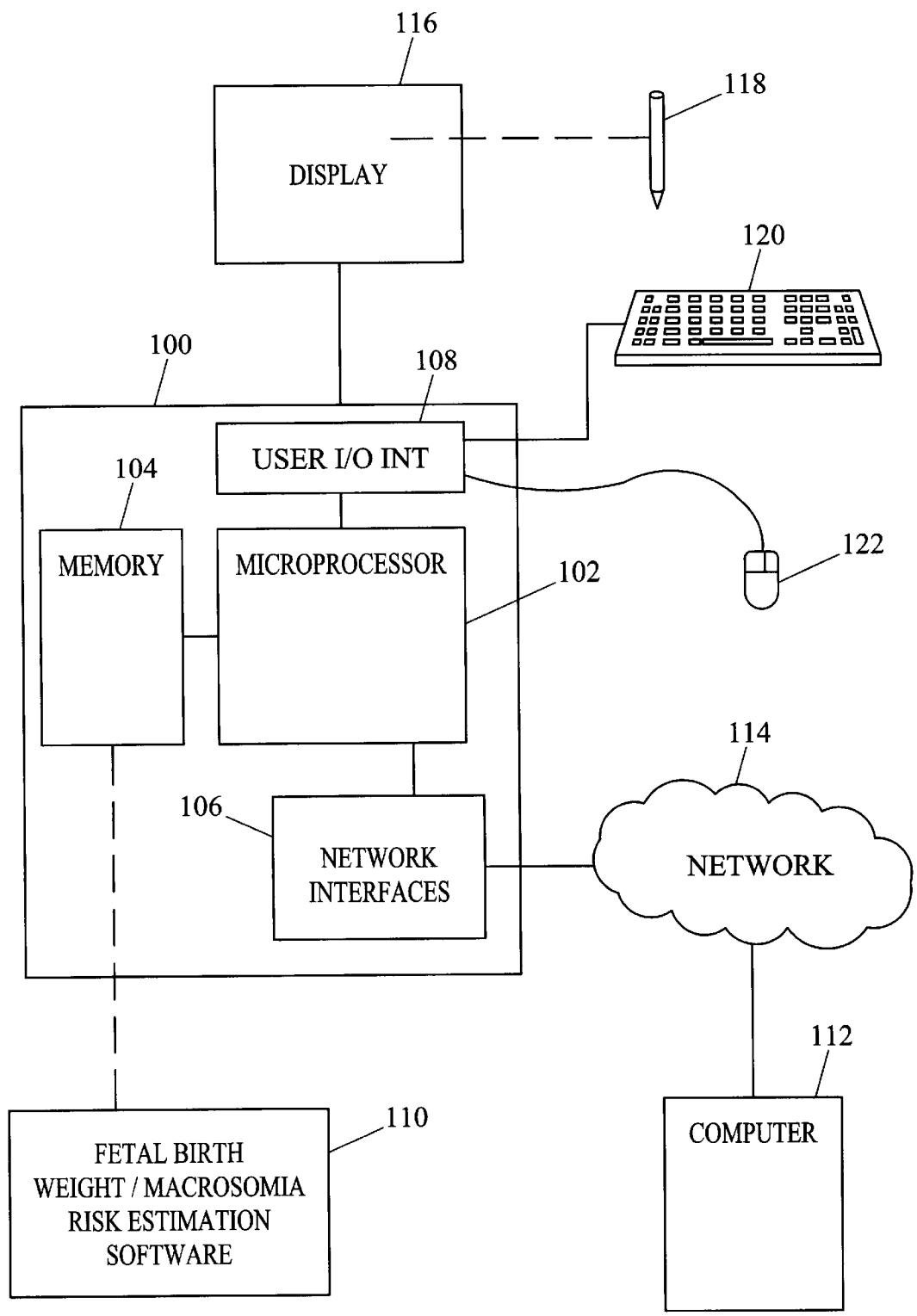
FIG. 1 is a block diagram of an exemplary operating environment for the methods and systems for estimating fetal weight at birth and risk of macrosomia according to an embodiment of the present invention.

The methods and systems of the invention for estimating fetal weight at birth and risk of macrosomia may be implemented in computer software designed to execute on any suitable computing platform, such as a personal computer, a hand held computer, a laptop computer, or a computer associated with an ultrasound device. FIG. 1 illustrates an exemplary operating environment for the fetal birth weight/macrosomia risk estimation software according to an embodiment of the present invention. Referring to FIG. 1, a computer 100 includes a microprocessor 102, memory 104, network interfaces 106, and user I/O interfaces 108. Microprocessor 102 may be any suitable microprocessor for executing stored instructions. An example of a microprocessor suitable for use with embodiments of the present invention is any of the Pentium family of processors available from Intel Corporation. A memory 104 stores instructions to be executed by microprocessor 102. In the illustrated example, memory 104 may store fetal birth weight/macrosomia risk estimation software 110.

Network interfaces 106 may allow computer 100 to communicate with one or more other computers 112 over network 114. For example, computer 100 may include web server software and computer 112 may include web client software. If computer 100 functions as a server, computer 100 may collect information from users via computer 112, calculate fetal birth weight and risk of macrosomia, and output the birth weight and risk estimate to computer 112 via network 114.

User I/O interface 108 manages communications with various user interface devices, such as display 116, pen 118, keyboard 120, and mouse 122. For example, if computer 100 is a desktop or laptop personal computer, computer 100 may receive input from a user via input devices 120 and 122 and display output to the user via display 116. If computer 100 is a hand held device, computer 100 may receive input from the user via pen 118 and display 116 and display output to the user via display 116.

Figure 2:
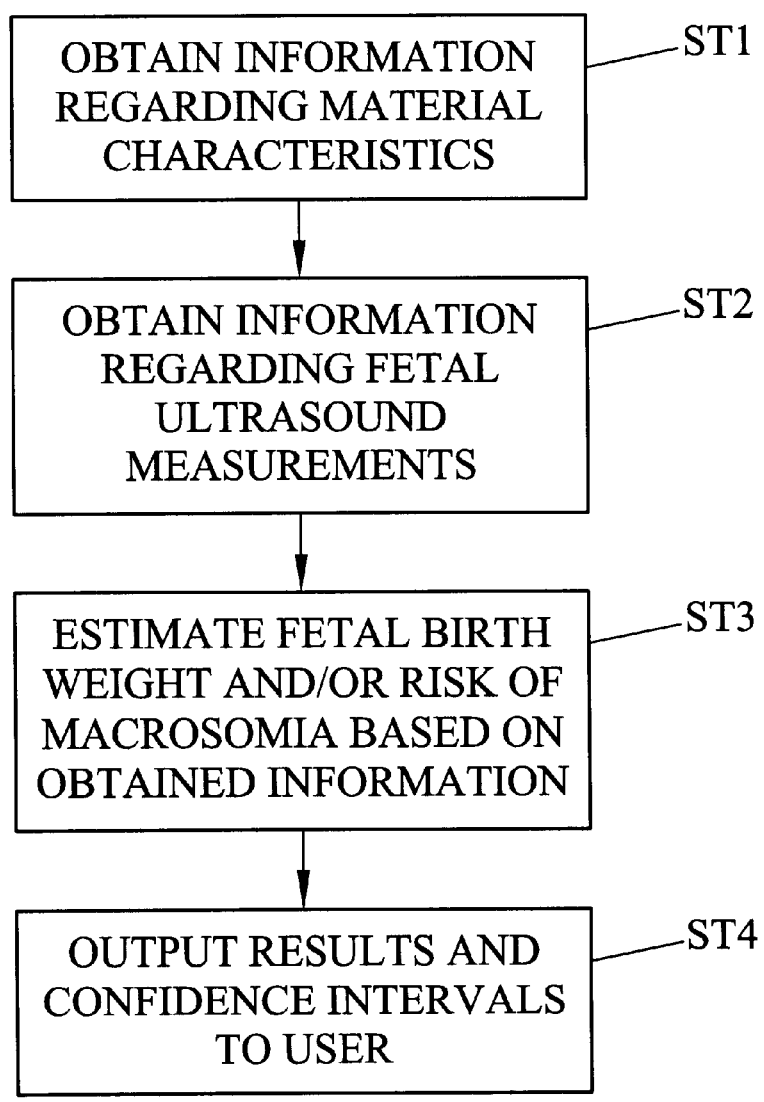
FIG. 2 is a flow chart illustrating the overall steps for predicting fetal weight at birth and risk of macrosomia according to an embodiment of the present invention.

FIG. 2 is a flow chart illustrating the overall steps performed by fetal birth weight/macrosomia risk estimation software 110 illustrated in FIG. 1. Referring to FIG. 2, in step ST1, fetal birth weight/macrosomia risk estimation software 110 obtains information regarding maternal characteristics for a fetus for which birth weight and risk of macrosomia is to be predicted. In step ST2, fetal birth weight/macrosomia risk estimation software 110 obtains information regarding fetal ultrasonographic measurements that may be available for a fetus for which birth weight and risk of macrosomia is to be predicted. Steps ST1 and ST2 may be performed using any of the input devices illustrated in FIG. 1. A detailed explanation of exemplary characteristics and measurements that may be obtained from a user will be explained below.

In step ST3, fetal birth weight/macrosomia risk estimation software 110 estimates fetal birth weight based on information obtained in steps ST1 and ST2. The estimation step involves selecting a fetal birth weight calculation equation from a hierarchy of stored equations based on available information. For example, if information regarding maternal characteristics is available but no ultrasound information is available, fetal birth weight/macrosomia risk estimation software 110 uses an equation that uses only maternal characteristics. Alternatively, if both maternal characteristics and ultrasound measurements are available, fetal birth weight/macrosomia risk estimation software 110 uses both maternal characteristics and ultrasound measurements to estimate fetal birth weight and/or risk of macrosomia. An exemplary hierarchy of equations for estimating fetal birth weight and macrosomic risk will be described in detail below.

In step ST4, fetal birth weight/macrosomia risk estimation software 110 outputs results to the user along with confidence intervals for the results. For fetal birth weight, the output may be the estimated weight of the fetus in grams along with a confidence interval for the calculation. For risk of macrosomia, the output may be a text string indicating the presence or absence of macrosomia and/or a percentage indicating the risk of macrosomia at the time of birth.

In order to perform steps ST1 and ST2 illustrated in FIG. 1, the user is preferably presented with a questionnaire requesting information regarding maternal characteristics and ultrasound measurements. The questionnaire may be presented to the user in paper format and input to fetal birth weight/macrosomic risk estimation software 110 by a patient, a relative, a friend, or a technician or other user, such as a physician or other type of obstetrical practitioner. Alternatively, fetal birth weight/macrosomia risk estimation software may be present the user with the questionnaire via display 116 or via computer network 114. The following is an example questionnaire that may be presented to a user to collect information for estimating fetal weight at birth and/or risk of macrosomia.

EXAMPLE QUESTIONNAIRE

1) How tall is the patient (enter height in either feet and inches or centimeters)?
2) What best characterizes the patient's racial/ethnic group?
   a) North American Caucasian
   b) South American Caucasian
   c) Western European Caucasian
   d) Eastern European Caucasian
   e) Australian/New Zealand Caucasian
   f) Russian/Asian Caucasian
   g) East Indian
   h) Pakistani
   i) North African
   j) African American (Black)

k) Japanese
l) Chinese
m) Vietnamese
n) Laotian
o) Cambodian
p) Taiwanese
q) Korean
r) Other Oriental
s) Filipino
t) Pacific Islander
u) American Indian
v) Other (specify)

3) How much did the patient weigh immediately before she became pregnant (enter weight in either pounds and ounces or kilograms)?

4) How much did the patient weigh at the time of her 26-week (six-month) check up (enter weight in either pounds and ounces or kilograms)?

5) When was the date of the patient's 26-week check-up when her weight was obtained (enter as MM/DD/YYY)?

6) What was the patient's weight at the time of her most recent check-up (enter weight in either pounds and ounces or kilograms)?

7) What was the date of the patient's most recent check-up when her weight was measured (enter as MM/DD/YYYY)?

8) What was the first day of the patient's last normal menstrual period (enter as MM/DD/YYYY)?

9) Did the patient's menstrual periods occur regularly each month before her last menstrual period (enter Yes/No)?

10) What was the interval at which the patient's menstrual periods occurred prior to becoming pregnant (enter either interval between the beginning of one menstrual period and the next in days, or "range from-to" if a known range in menstrual intervals was present, or "variable" if no consistent pattern was present)?

11) Was the patient using hormonal contraception when she became pregnant (enter Yes/No)?
If the answer is Yes, was the contraceptive method either:
 a) Oral Contraceptives (birth control pills)
 b) Depo-Provera (a progestin administered by injection, generally every 3 months)
 c) Norplant (an implantable progestational contraceptive)
 d) Lunelle (an injectable monthly combination estrogen/progestin contraceptive)
 e) Nuva-Ring (an estrogen/progestin-containing vaginal ring worn for three weeks out of four)
 f) Mirena IUD (progestin-containing intrauterine device)
 g) Ortho-Evra estrogen/progestin contraceptive Patch
 h) Other hormonal contraceptive (specify)

12) What was the date when the patient's first obstetrical ultrasound examination was performed (enter date as MM/DD/YYYY)?

13) How many weeks pregnant did the patient's first ultrasound examination say that she was on the date it was performed (enter number of weeks as either a decimal number, e.g., 8.4 weeks, or as number of weeks plus number of days, e.g., 8 weeks 3 days)?

14) Did the patient have either an amniocentesis or chorionic villus sampling performed during this pregnancy (enter Yes/No)?
 a) If she had either an amniocentesis or chorionic villus sampling performed, were the results normal (enter either Normal/Abnormal)?
 b) If the results were Abnormal, what was the type of abnormality (specify)?

15) Does the patient have a personal history of diabetes mellitus (a high blood sugar problem) (enter Yes/No)?

16) At some time during the patient's pregnancy, she should have had a 1-hour 50-gram oral glucose screening test to rule out diabetes mellitus:
 a) What was the result of the 1-hour 50-gram glucose screening test result (enter as either [gm/dL] or [mg %])?
 b) What was the date when the 1-hour 50-gram glucose screening test was performed (enter as MM/DD/YYYY)?

17) Did the patient have a formal 3-hour 100-gm glucose tolerance test performed during this pregnancy (enter Yes/No)?
 a) If she did have a 3-hour 100-gm glucose tolerance test performed, what was the date (enter as MM/DD/YYYY)?
 b) If she did have a 3-hour 1 00-gm glucose tolerance test performed, what were the results (enter "fasting blood sugar result", "1-hour blood sugar result", "2-hour blood sugar result", and "3-hour blood sugar result")?

18) Do you know the sex of the patient's fetus (enter male, female, or unknown)?

19) How many prior babies has the patient delivered (enter number of prior babies)?

20) What was the date of the patient's most recent prior delivery (enter as MM/DD/YYYY)?

21) How many weeks pregnant was the patient when she delivered her last baby (enter the number of weeks and days that she was pregnant at the time of her last delivery)?

22) What was the weight of the patient's last baby at the time of delivery (enter weight in either pounds and ounces or kilograms)?

23) What was the patient's last baby's sex (enter male, female, or unknown)?

24) Were there any congenital anomalies in the patient's last baby (enter Yes/No)?
 a) If the answer is Yes, specify the type of abnormality (enter either None or specify type).

25) What was the patient's most recent blood hemoglobin concentration (enter hemoglobin level in grams per deciliter, or [gm/dl])?

26) When was the patient's most recent hemoglobin level obtained (enter as MM/DD/YYY)?

27) When was the patient's most recent obstetrical ultrasound examination (enter as MM/DD/YYYY)?

28) What was the abdominal circumference measurement (AC measurement) of the fetus's abdomen on the date of the most recent ultrasound examination (enter numerical result in mm)?

29) What was the head circumference measurement (HC measurement) of the fetus's head on the date of the most recent ultrasound examination (enter numerical result in mm)?

30) What was the biparietal diameter measurement (BPD measurement) of the fetus's head on the date of the most recent ultrasound examination (enter numerical result in mm)?

31) What was the femur length measurement (FL measurement) of the fetus's thigh on the date of the most recent ultrasound examination (enter numerical result in mm)?
32) Were there any abnormalities discovered at the time of any of the ultrasound studies that were performed for this patient (enter Yes/No)?
   a) If there were abnormalities discovered, what were they (enter either None or specify type of abnormality)?
33) Does the patient have chronic hypertension (high blood pressure) (enter Yes/No)?
34) Does the patient have either pregnancy-induced hypertension or pre-eclampsia (enter Yes/No)?
35) Does the patient have any other major medical illnesses (enter either None or specify type)?
36) Does the patient use any glucocorticoid medications (examples: Prednisone, Prednisolone, Medroxyprednisolone, Cortisone, Hydrocotisone, Dexamethasone, or Betamethasone) (enter Yes/No)?
37) Does the patient use Terbutaline on a chronic basis (enter Yes/No)?
38) Does the patient take any other medications on a chronic basis (enter Yes/ No)?
   a) If the answer is Yes, what type (specify)?
39) Does the patient smoke cigarettes (enter Yes/No)?
   a) If Yes, how many cigarettes are smoked per day during pregnancy (enter number)?
40) Does the patient use illicit drugs (enter Yes/No)?
   a) If the answer is Yes, what type (specify)?
41) At what altitude does the patient live (enter altitude above mean sea level for the city or town in either feet or meters)?
42) How tall is the father of the baby (enter his height in either feet and inches or cm)?
43) Was there ovum donation associated with the current pregnancy (enter Yes/No)?
44) Was there sperm donation associated with the current pregnancy (enter Yes/No)?

The present invention is not limited to obtaining patient information using the questionnaire above. Questions may be modified, added or deleted without departing from the scope of the invention.

Abbreviations and Equations

Fetal birth weight/macrosomia risk estimation software 110 preferably utilizes a hierarchy of equations in order to estimate fetal weight at birth and/or risk of macrosomia. The operation of fetal birth weight/macrosomic risk estimation software 110 will be explained with regard to the flow charts illustrated in FIGS. 3A–4B. The flow charts reference equations by numbers. All of the variables and terms that are incorporated in each of the different equations are unique predictors of fetal weight that are specifically and uniquely operational within the context of each equation. Thus, each variable and term in each of the different equations explains an independent portion of the variance in fetal birth weight that the other variables and terms in each individual equation cannot. As such, and within a hierarchy of predictive accuracy that depends exclusively upon the type and quality of maternal and fetal ultrasonographic information that is available, each equation stands alone in its ability to predict fetal weight at birth. Examples of equations and abbreviations used in the equations and the flow charts illustrated in FIGS. 3A–4B are as follows:

BWT = Patient's predicted birth weight, in grams

Day0 = Due date (expected date of confinement) minus 280 = Date of the first day of the last normal menstrual period = Conception date minus 14 days Target Date = date for which birth weight prediction and/or fetal macrosomia risk prediction is desired GA = Gestational age (days since Day0) on target date AC = Fetal abdominal circumference as measured by ultrasonography, in mm HC = Fetal head circumference in as measured by ultrasonography, in mm BPD = Fetal biparietal diameter in as measured by ultrasonography, in mm FL = Fetal femur length in as measured by ultrasonography, in mm DeltaUS = Number of elapsed days between fetal ultrasonographic measurements and target date Parity = Number of prior babies delivered Height = Patient's height, in cm Hgb = Patient's third trimester venous hemoglobin concentration, in grams per deciliter Prior = Birth weight of patient's previous term newborn, in grams PPW = The patient's weight immediately prior to the current pregnancy, in kg $Wt_{Last}$ = The last recorded weight for the patient for which an associated gestational age is known, in kg $GA_{Last}$ = The gestational age (days since Day0) on which $Wt_{Last}$ was measured $Wt_{2ndLast}$ = The $2^{nd}$-last recorded weight of the patient (i.e., the weight immediately preceding $Wt_{Last}$), in kg $GA_{2ndLast}$ = The gestational age (days since Day0) on which $Wt_{2ndLast}$ was measured $Wt_{182}$ = Patient's weight 182 days after Day0, in kg $Rate_{3rd}$ = Patient's weight gain rate during the $3^{rd}$ trimester, in kg per day Equation 1: BWT=−4147+(9.693×AC)+(11.92×HC)+(21.21×DeltaUS)+(3.429×GA×$Rate_{3rd}$×[Parity+1])

Equation 2: BWT=−4280+(9.633×AC)+(12.48×HC)+(21.66×DeltaUS)+(0.1822×GA×[Parity+1])

Equation 3: BWT=−3468+(10.95×AC)+(28.83×BPD)+(19.86×DeltaUS)+(0.00007464×GA×Height×$Wt_{182}$)+(3.336×GA×$Rate_{3rd}$×[Parity+1])

Equation 4: BWT=−3337+(10.96×AC)+(27.61×BPD)+(20.16×DeltaUS)+(0.0001027×GA×Height×$Wt_{182}$)

Equation 5: BWT=−3726+(11.17×AC)+(33.18×BPD)+(21.14×DeltaUS)+(3.817×GA×$Rate_{3rd}$×[Parity+1])

Equation 6: BWT=−3814+(11.27×AC)+(34.17×BPD)+(21.59×DeltaUS)+(0.1970×GA×[Parity+1])

Equation 7: BWT=−2495+(11.87×AC)+(18.39×FL)+(18.79×DeltaUS)+(0.00008700×GA× Height×$Wt_{182}$)+(3.260×GA×$Rate_{3rd}$×[Parity+1])

Equation 8: BWT=−2388+(11.87×AC)+(17.23×FL)+(19.07×DeltaUS)+(0.0001142×GA×Height×$Wt_{182}$)

Equation 9: BWT=−2644+(12.38×AC)+(21.58×FL)+(20.17×DeltaUS)+(3.797×GA×$Rate_{3rd}$×[Parity+1])

Equation 10: BWT=−2547+(12.52×AC)+(21.37×FL)+(20.88×DeltaUS)

Equation 11: BWT=−1627+(13.18×AC)+(16.23×DeltaUS)+(0.00009964×GA×Height×$Wt_{182}$)+(3.173×GA×$Rate_{3rd}$×[Parity+1])

Equation 12: BWT=−1576+(13.10×AC)+(16.66×DeltaUS)+(0.0001254×GA×Height×$Wt_{182}$)

Equation 13: $BWT = -2469 + (13.09 \times AC) + (16.17 \times DeltaUS) + (0.02625 \times GA \times Height) + (3.812 \times GA \times Rate_{3rd} \times [Parity+1])$ Equation 14: $BWT = -2501 + (13.28 \times AC) + (16.51 \times DeltaUS) + (0.02647 \times GA \times Height) + (0.1877 \times GA \times [Parity+1])$ Equation 15: $BWT = -4260 + (15.57 \times HC) + (27.33 \times FL) + (17.55 \times DeltaUS) + (0.00008659 \times GA \times Height \times Wt_{182}) + (2.902 \times GA \times Rate_{3rd} \times [Parity+1])$ Equation 16: $BWT = -4225 + (15.80 \times HC) + (26.12 \times FL) + (17.95 \times DeltaUS) + (0.0001112 \times GA \times Height \times Wt_{182})$ Equation 17: $BWT = -4639 + (17.37 \times HC) + (27.90 \times FL) + (18.97 \times DeltaUS) + (3.326 \times GA \times Rate_{3rd} \times [Parity+1])$ Equation 18: $BWT = -4666 + (17.97 \times HC) + (27.06 \times FL) + (19.79 \times DeltaUS)$ Equation 19: $BWT = -3840 + (12.69 \times HC) + (27.33 \times BPD) + (15.11 \times DeltaUS) + (0.00009689 \times GA \times Height \times Wt_{182}) + (2.898 \times GA \times Rate_{3rd} \times [Parity+1])$ Equation 20: $BWT = -3810 + (13.25 \times HC) + (25.21 \times BPD) + (15.58 \times DeltaUS) + (0.0001210 \times GA \times Height \times Wt_{182})$ Equation 21: $BWT = -4222 + (14.33 \times HC) + (28.71 \times BPD) + (16.56 \times DeltaUS) + (3.392 \times GA \times Rate_{3rd} \times [Parity+1])$ Equation 22: $BWT = -4234 + (15.44 \times HC) + (26.06 \times BPD) + (17.40 \times DeltaUS)$ Equation 23: $BWT = -3383 + (18.85 \times HC) + (13.95 \times DeltaUS) + (0.00009838 \times GA \times Height \times Wt_{182}) + (2.757 \times GA \times Rate_{3rd} \times [Parity+1])$ Equation 24: $BWT = -3388 + (18.93 \times HC) + (14.49 \times DeltaUS) + (0.0001213 \times GA \times Height \times Wt_{182})$ Equation 25: $BWT = -3764 + (20.88 \times HC) + (15.40 \times DeltaUS) + (3.239 \times GA \times Rate_{3rd} \times [Parity+1])$ Equation 26: $BWT = -3816 + (21.37 \times HC) + (16.30 \times DeltaUS)$ Equation 27: $BWT = -3492 + (45.16 \times BPD) + (30.75 \times FL) + (16.35 \times DeltaUS) + (0.00009699 \times GA \times Height \times Wt_{182}) + (3.453 \times GA \times Rate_{3rd} \times [Parity+1])$ Equation 28: $BWT = -3326 + (44.25 \times BPD) + (29.95 \times FL) + (16.53 \times DeltaUS) + (0.0001266 \times GA \times Height \times Wt_{182})$ Equation 29: $BWT = -4277 + (45.49 \times BPD) + (29.51 \times FL) + (16.18 \times DeltaUS) + (0.02549 \times GA \times Height) + (4.073 \times GA \times Rate_{3rd} \times [Parity+1])$ Equation 30: $BWT = -4352 + (47.04 \times BPD) + (28.85 \times FL) + (16.46 \times DeltaUS) + (0.02596 \times GA \times Height) + (0.2127 \times GA \times [Parity+1])$ Equation 31: $BWT = -1028 + (52.61 \times FL) + (11.38 \times DeltaUS) + (0.0001424 \times GA \times Height \times Wt_{182}) + (3.221 \times GA \times Rate_{3rd} \times [Parity+1])$ Equation 32: $BWT = -907.5 + (51.28 \times FL) + (11.60 \times DeltaUS) + (0.0001693 \times GA \times Height \times Wt_{182})$ Equation 33: $BWT = -2183 + (50.45 \times FL) + (10.98 \times DeltaUS) + (0.03900 \times GA \times Height) + (4.145 \times GA \times Rate_{3rd} \times [Parity+1])$ Equation 34: $BWT = -1993 + (50.91 \times FL) + (11.66 \times DeltaUS) + (0.03719 \times GA \times Height)$ Equation 35: $BWT = -2330 + (56.44 \times BPD) + (11.67 \times DeltaUS) + (0.0001188 \times GA \times Height \times Wt_{182}) + (3.372 \times GA \times Rate_{3rd} \times [Parity+1])$ Equation 36: $BWT = -3444 + (55.51 \times BPD) + (11.58 \times DeltaUS) + (0.03485 \times GA \times Height) + (4.142 \times GA \times Rate_{3rd} \times [Parity+1])$ Equation 37: $BWT = -2189 + (55.16 \times BPD) + (11.93 \times DeltaUS) + (0.0001475 \times GA \times Height \times Wt_{182})$ Equation 38: $BWT = -3558 + (56.89 \times BPD) + (11.93 \times DeltaUS) + (0.03529 \times GA \times Height) + (0.2334 \times GA \times [Parity+1])$ Equation 39: $BWT = -3651 + (70.47 \times BPD) + (14.60 \times DeltaUS) + (0.1853 \times Prior)$ Equation 40: $BWT = -1212 + GA \times [13.69 + (0.2419 \times Gender\#) + (0.0002004 \times Height \times Wt_{182}) + (11.59 \times Rate_{3rd})] - (40.75 \times Hgb) + (0.1598 \times Prior)$ Equation 41: $BWT = -1316 + GA \times [14.50 + (0.2574 \times Gender\#) + (0.0002175 \times Height \times Wt_{182})] - (39.33 \times Hgb) + (0.1697 \times Prior)$ Equation 42: $BWT = -2214 + GA \times [17.49 + (0.2607 \times Gender\#) + (12.03 \times Rate_{3rd})] + (0.1987 \times Prior)$ Equation 43: $BWT = -2387 + GA \times [18.72 + (0.2767 \times Gender\#)] + (0.2179 \times Prior)$ Equation 44: $BWT = -1727 + GA \times [17.44 + (0.2346 \times Gender\#) + (0.0002106 \times Height \times Wt_{182}) + (3.350 \times Rate_{3rd} \times \{Parity+1\})] - (39.05 \times Hgb)$ Equation 45: $BWT = -1547 + GA \times [17.13 + (0.2322 \times Gender\#) + (0.0002270 \times Height \times Wt_{182})] - (40.93 \times Hgb)$ Equation 46: $BWT = -1689 + GA \times [13.19 + (0.2556 \times Gender\#) + (0.03884 \times Height) + (4.072 \times Rate_{3rd} \times \{Parity+1\})] - (33.88 \times Hgb)$ Equation 47: $BWT = -1611 + GA \times [12.68 + (0.2593 \times Gender\#) + (0.04144 \times Height) + (0.1755 \times \{Parity+1\})] - (33.40 \times Hgb)$ Equation 48: $BWT = -1643 + GA \times [15.92 + (0.2441 \times Gender\#) + (0.0001998 \times Height \times Wt_{182}) + (1.552 \times Rate_{3rd} \times \{Parity+1\})]$ Equation 49: $BWT = -1677 + GA \times [15.87 + (0.2596 \times Gender\#) + (0.0002059 \times Height \times Wt_{182}) + (0.1779 \times \{Parity+1\})]$ Equation 50: $BWT = -1553 + GA \times [11.55 + (0.2614 \times Gender\#) + (0.03916 \times Height) + (1.882 \times Rate_{3rd} \times \{Parity+1\})]$ Equation 51: $BWT = -1576 + GA \times [11.92 + (0.2750 \times Gender\#) + (0.03629 \times Height) + (0.2123 \times \{Parity+1\})]$ Equation 52: $BWT = GA \times [10.16 + (0.3596 \times Gender\#) + (0.0001201 \times Height \times Wt_{182}) + (4.297 \times Rate_{3rd})]$ Equation 53: $BWT = GA \times [10.43 + (0.3783 \times Gender\#) + (0.0001327 \times Height \times Wt_{182})]$ Equation 54: $BWT = GA \times [(0.4209 \times Gender\#) + (0.07123 \times Height) + (3.971 \times Rate_{3rd})]$ Equation 55: $BWT = GA \times [(0.3920 \times Gender\#) + (0.07303 \times Height)]$ Equation 56: $BWT = GA \times [8.823 + (0.0003013 \times Height \times Wt_{182})]$ Equation 57: $BWT = -1243 + GA \times [(0.2741 \times Gender\#) + (0.1042 \times Height)]$ Equation 58: $BWT = -1770 + GA \times [16.25 + (0.0001676 \times Height \times Wt_{182}) + (4.826 \times Rate_{3rd} \times \{Parity+1\})]$ Equation 59: $BWT = -1469 + GA \times [15.44 + (0.0002050 \times Height \times Wt_{182})]$ Equation 60: $BWT = GA \times [(0.07227 \times Height) + (5.410 \times Rate_{3rd} \times \{Parity+1\})]$ Equation 61: $BWT = -1874 + (GA \times 18.77)$ In the equations listed above, numeric constants are included to facilitate calculation of fetal weight at birth and risk of macrosomia. These constants were obtained based on experimental data. However, the present invention is not limited to using these exact constants. These constants are merely illustrated to illustrate the best mode known for practicing the invention at the time of filing. One or more of the numeric constants in each equation may be changed without departing from the scope of the invention.

Fetal Birth Weight/Macrosomic Risk Estimation Program Flow

Figure 3A:
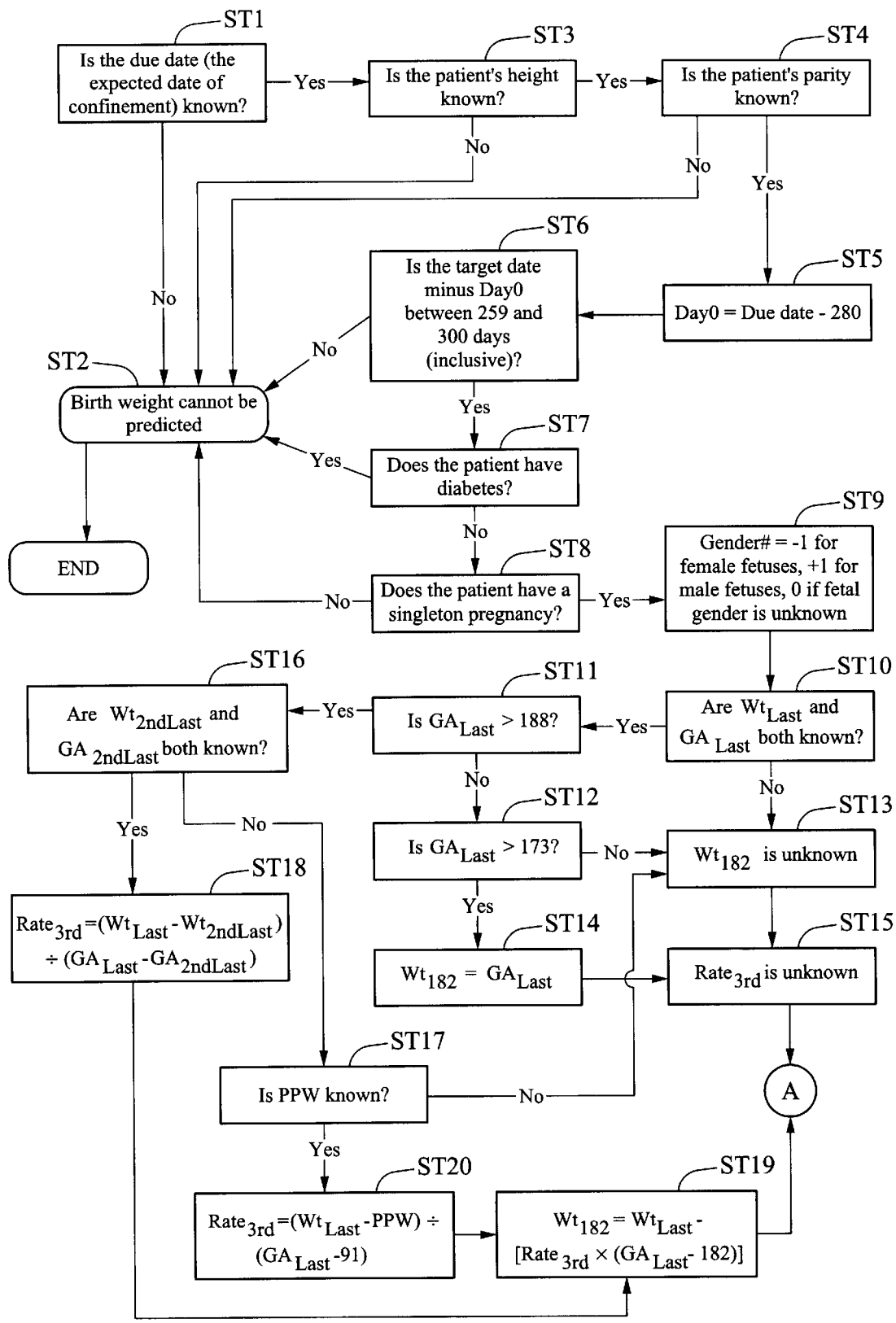
FIGS. 3A–3G are flow charts illustrating exemplary steps for estimating fetal weight at birth according to an embodiment of the present invention.

FIGS. 3A–4B illustrate exemplary steps that may be performed by fetal birth weight/macrosomia risk estimation software 110 in estimating fetal birth weight and/or risk of macrosomia. Referring to FIG. 3A, in step ST1, the program determines whether the expected due date is known. The expected due date may be determined using any suitable method. For example, one method for calculating the expected due date is adding 280 days to the first day of the patient's last normal menstrual period. Another method is adding thirty-eight weeks to the fertilization date. Yet another method for estimating the expected due date is to use ultrasound measurements to determine the approximate age of the fetus and to predict the expected due date based on the age. If the expected due date is not known, control proceeds to step ST2 where the birth weight cannot be predicted. After this step, processing for estimating fetal birth weight ends.

If the expected due date is known, control proceeds to step ST3 where the program determines whether the patient's (i.e., the mother's) height is known. If the patient's height is not known, control proceeds to step ST2 where the program determines that birth weight cannot be predicted. If the patient's height is known, control proceeds to step ST4 where the program determines whether the patient's parity is known. As indicated above, the term parity refers to the number of prior children to which the patient has given birth. If the patient's parity is not known, control proceeds to step ST2, where the program determines that birth weight cannot be predicted.

If, on the other hand, the program determines that the patient's parity is known, control proceeds to step ST5 where the program calculates the value for a variable referred to herein as Day0 (defined above). In step ST6, the program calculates whether the target date minus Day0 is between 259 and 300 days inclusive. As used herein, the term "target date" refers to the date for which birth weight or risk of macrosomia will be predicted. If the program determines that the target date minus Day0 is not between 259 and 300 days inclusive, control proceeds to step ST2 where the program determines that birth weight cannot be predicted.

If the program determines that the target date minus Day0 is between 259 and 300 days inclusive, control proceeds to step ST7 where the program determines whether the patient has diabetes. If the patient has diabetes, control proceeds to step ST2 where the program determines that birth weight cannot be predicted. If the program determines that the patient does not have diabetes, control proceeds to step ST8 where the program determines whether the patient has a singleton pregnancy. If the program determines that the patient does not have a singleton pregnancy, control proceeds to step ST2 where the program determines that birth weight cannot be predicted.

If the program determines that the patient does have a singleton pregnancy, control proceeds to step ST9 where the program stores a value indicative of fetal gender. In the illustrated example, a negative 1 is stored for female fetuses, a positive 1 is stored for male fetuses, and a 0 is stored if fetal gender is unknown.

In step ST10, the program determines whether the last recorded weight of the patient and the gestational age at the time of the last recorded weight are both known. As indicated above in the definitions section, the gestational age is the days since Day0 on which the patient's weight was last measured. If the last recorded weight of the patient and the gestational age at the time of the last recorded weight are not both known, control proceeds to step ST13, where the program determines that the patient's weight at 182 days is unknown, and to step ST15, where the program determines that the patient's third trimester weight gain rate is unknown. Control then proceeds to the flow chart illustrated in FIG. 3B through connector A in FIG. 3A.

If in step ST10, the program determines that the last recorded weight of the patient and the gestational age at the time of the last recorded weight are both known, control proceeds to step ST11 where it is determined whether the gestational age of the fetus on the day on which the patient's weight was last measured is greater than 188 days. If the gestational age is not greater than 188 days control proceeds to step ST12 where the program determines whether the gestational age on the day on which the patient's weight was last measured is greater than 173 days. If the age is not greater than 173 days control proceeds to step ST13 where it is determined that the patient's weight 182 days after Day0 is not known.

If in step ST12, the program determines that the age was between 173 and 188 days at the last weight measurement, control proceeds to step ST14 where the program sets the weight at 182 days to the patient's last weight measurement. Control then proceeds to step ST15 where the program determines that the rate of weight gain during the third trimester is unknown. If in step ST11, the program determines that the gestational age on the day of the patient's last weight measurement is greater than 188 days, control proceeds to step ST16 where the program determines whether the patient's second-to-last weight measurement and the corresponding gestational age are both known. If both are not known, control proceeds to step ST17 where the program determines whether the patient's pre-pregnancy weight is known. If the patient's pre-pregnancy weight is not known, control proceeds to steps ST13 and ST15 where the program determines that the patient's weight at 182 days is not known and that the patient's rate of weight gain during the third trimester is not known. If rate of weight gain during the third trimester and weight at 182 days are both unknown, control proceeds to the flow chart illustrated in FIG. 3B through connector A in FIG. 3A.

Returning to step ST16, if the second-to-last weight measurement and the corresponding gestational age are both known, control proceeds to step ST18, where the program calculates the rate of weight gain during the third trimester. Control then proceeds to step ST19 where the program uses the rate of third trimester weight gain calculated in step ST18 to calculate the patient's weight corresponding to a gestational age of 182 days (hereinafter, "patient's weight at 182 days"). Similarly, in step ST17, if the pre-pregnancy weight is known, in step ST20, the rate of weight gain during the third trimester is calculated using the pre-pregnancy weight and control proceeds to step ST19 where the patient's weight at 182 days is calculated.

Figure 3B:
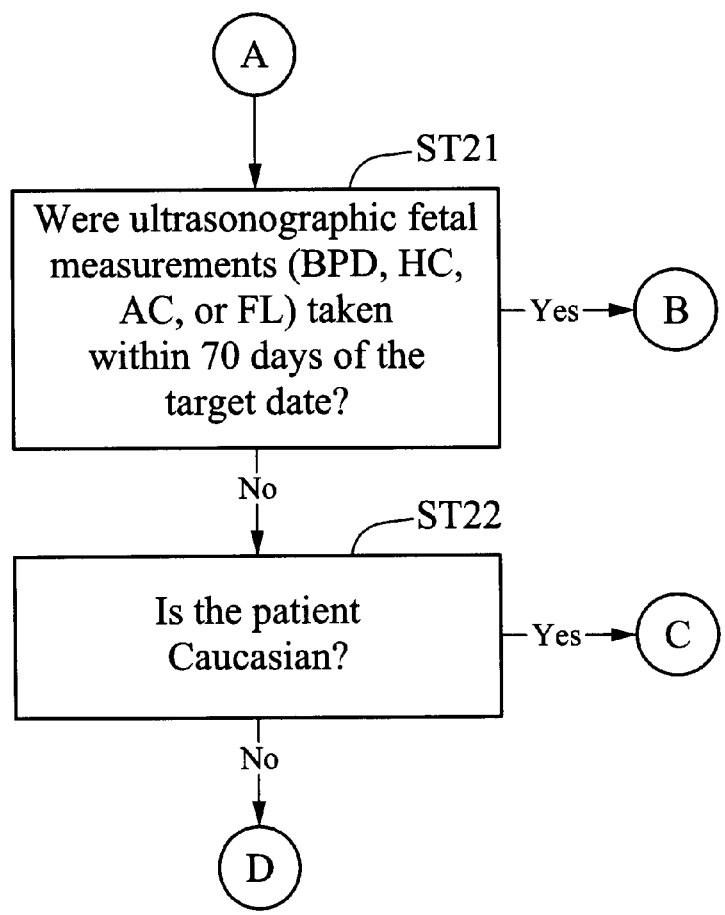

Once the program either calculates the weight at 182 days and the third trimester weight gain rate or determines that the weight or the third trimester weight gain rate, or both, are unknown, control proceeds to the flow chart illustrated in FIG. 3B through connecter A. Referring to FIG. 3B, in step ST21, the program determines whether any or all of the following four ultrasound measurements were taken within seventy days of the target date: fetal biparietal diameter (BPD), fetal head circumference (HC), fetal abdominal circumference (AC), and fetal femur length (FL). If any or all of these measurements were taken within seventy days of the target date, control proceeds to the flow chart illustrated in FIG. 3C through connector B in FIG. 3B. If any or all of the measurements in step ST21 were not taken within seventy days of the target date, control proceeds to step ST22 where the program determines whether the patient is Caucasian. If the patient is Caucasian, control proceeds to the flow chart illustrated in FIG. 3F through connector C in FIG. 3B. If the program determines that the patient is not Caucasian, control proceeds to the flow chart illustrated in FIG. 3G through connector D illustrated in FIG. 3B.

Figure 3C:
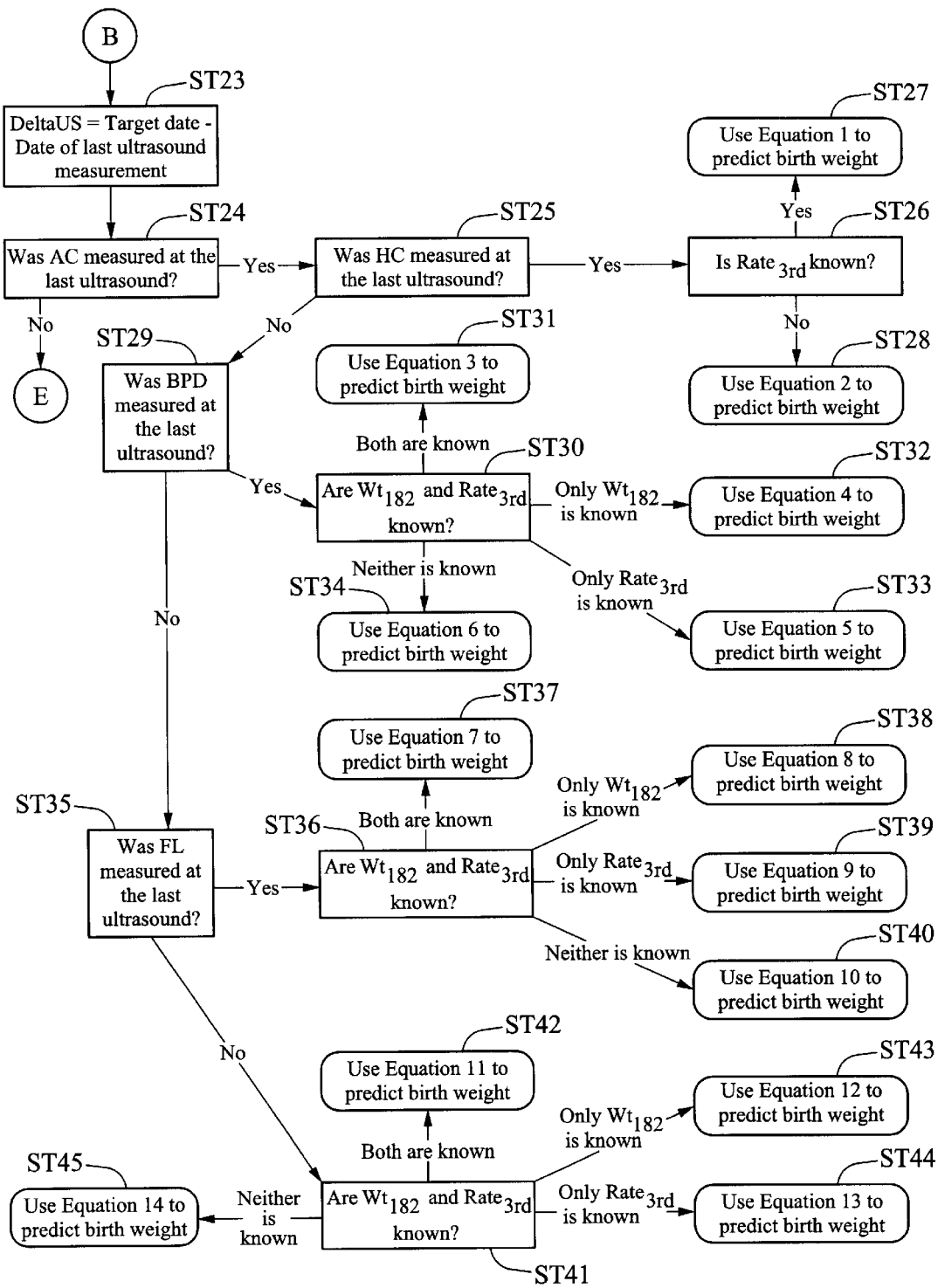

FIG. 3C illustrates exemplary steps that may be performed by fetal birth weight calculation/macrosomia risk estimation software 110 illustrated in FIG. 1 if certain ultrasound measurements were taken within seventy days of the target date. Referring to FIG. 3C, in step ST23, the program computes a quantity DeltaUS, which indicates the number of days that elapse between the fetal ultrasonographic measurements and the target date. In step ST24, the program determines whether fetal abdominal circumference (AC) was measured at the last ultrasound. If fetal abdominal circumference (AC) was not measured at the last ultrasound, control proceeds to the flow chart illustrated in FIG. 3D through connector E in FIG. 3C.

In step ST24, if the program determines that fetal abdominal circumference (AC) was measured at the last ultrasound, control proceeds to step ST25 where the program determines whether the fetal head circumference (HC) was measured at the last ultrasound. If the fetal head circumference (HC) was measured at the last ultrasound, control proceeds to step ST26 where the program determines whether the rate of weight gain during the third trimester is known. If the rate of weight gain during the third trimester is known, the program uses Equation 1 listed above to predict birth weight. In step ST26, if the program determines that the rate of weight gain during the third trimester is not known, program uses Equation 2 listed above to predict birth weight (step ST28).

Returning to step ST25, if the fetal head circumference (HC) was not measured at the last ultrasound, control proceeds to step ST29 where the program determines whether the fetal biparietal diameter (BPD) was measured at the last ultrasound. If biparietal diameter was measured at the last ultrasound, control proceeds to step ST30 where the program determines whether the patient's weight at 182 days and the rate of weight gain during the third trimester are known. If both are known, in step ST31, the program uses Equation 3 to predict birth weight. If only the patient's weight at 182 days is known but not the rate of maternal weight gain during the third trimester, the program uses Equation 4 to predict birth weight (step ST32). If only the rate of weight gain during the third trimester is known but not the patient's weight at 182 days, the program uses Equation 5 to predict birth weight (step ST33). If neither parameter is known, control proceeds to step ST34 where the program uses Equation 6 to predict birth weight.

Returning to step ST29, if the fetal biparietal diameter (BPD) was not measured at the last ultrasound, control proceeds to step ST35 where the program determines whether the fetal femur length (FL) was measured at the last ultrasound. If the fetal femur length (FL) was measured at the last ultrasound, control proceeds to step ST36 where the program determines whether rate of weight gain during the third trimester and the patient's weight at 182 days are known. If both parameters are known, in step ST37, the program uses Equation 7 to predict birth weight. If only the patient's weight at 182 days is known, program uses Equation 8 to predict birth weight (step ST38). If only the rate of weight gain during the third trimester is known, the program uses Equation 9 to predict birth weight (step ST39). Finally, if neither the patient's weight at 182 days nor rate of weight gain during the third trimester is known, the program uses Equation 10 to predict birth weight (step ST40).

Returning again to step ST35, if the fetal femur length (FL) was not measured at the last ultrasound, control proceeds to step ST41 where the program determines whether the patient's weight at 182 days and rate of weight gain during the third trimester are known. If both parameters are known, in step ST42, the program uses Equation 11 to predict birth weight. If only the patient's weight at 182 days is known, the program uses Equation 12 to predict birth weight (step ST43). If only the rate of weight gain during the third trimester is known, the program uses Equation 13 to predict birth weight (step ST44). Finally, if neither parameter is known, the program uses Equation 14 to predict birth weight (step ST45).

Figure 3D:
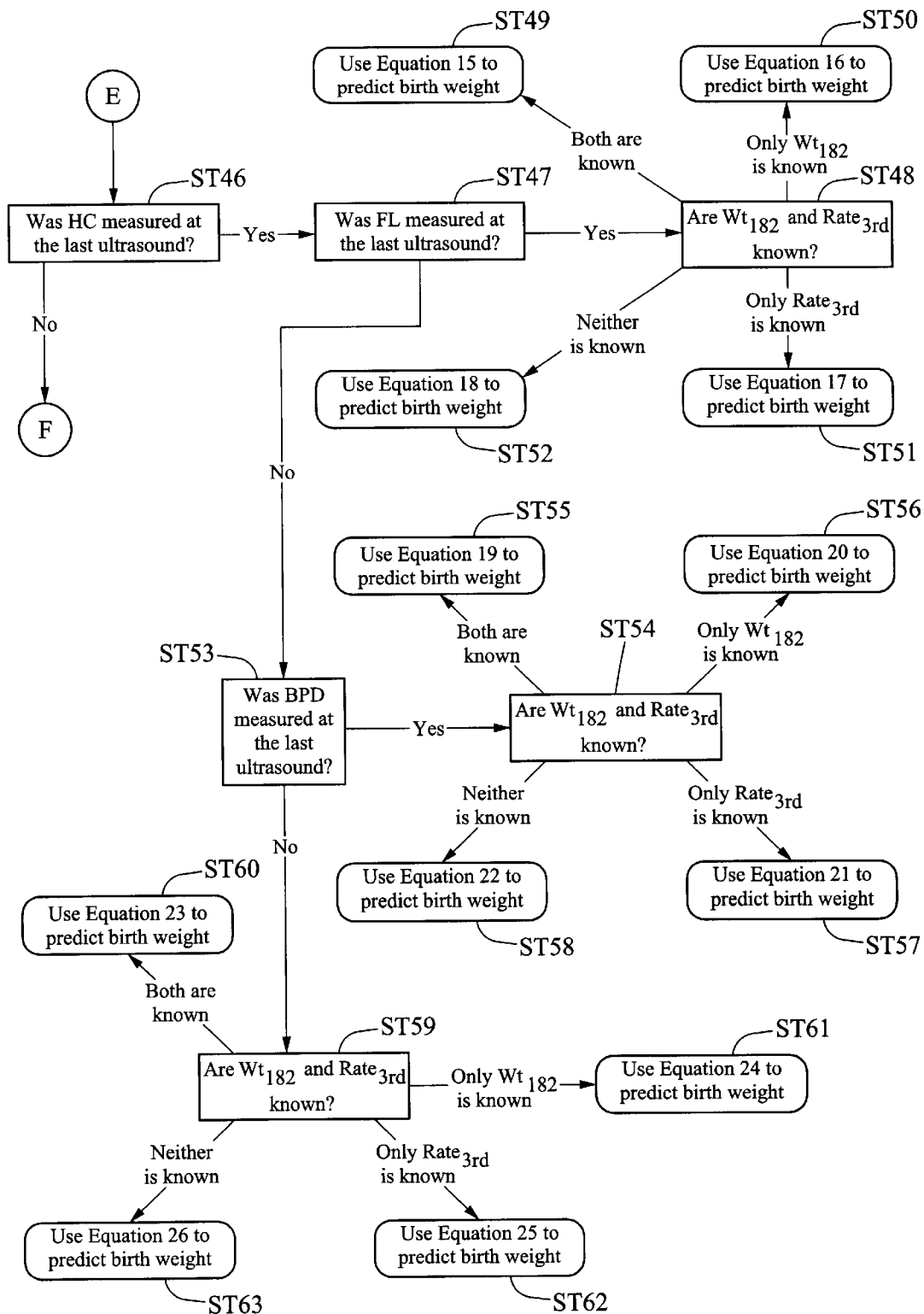

FIG. 3D illustrates exemplary steps performed by fetal birth weight/macrosomia risk estimation software 110 in estimating fetal birth weight if the fetal abdominal circumference (AC) was not measured at the last ultrasound. Entry is via connector E from the preceding flow sheet 3C at ST24.

Referring to FIG. 3D, in step ST46, the program determines whether the fetal head circumference (HC) was measured at the last ultrasound. If the fetal head circumference (HC) was not measured at the last ultrasound, control proceeds to the flow chart illustrated in FIG. 3E through connector F. If the fetal head circumference (HC) was measured at the last ultrasound, control proceeds to step ST47 where the program determines whether the fetal femur length (FL) was measured at the last ultrasound. If the fetal femur length (FL) was measured at the last ultrasound, control proceeds to step ST48 where the program determines whether the patient's weight at a gestational age of 182 days and rate of weight gain during the third trimester are known. If both are known, the program uses Equation 15 to predict birth weight (step ST49). If only the patient's weight at 182 days is known, the program uses Equation 16 to predict birth weight (step ST50). If only the rate of weight gain during the third trimester is known, the program uses Equation 17 to predict birth weight (step ST51). Finally, if neither of the parameters is known, the program uses Equation 18 to predict birth weight (step ST52).

Returning to step ST47, if the fetal femur length (FL) was not measured at the last ultrasound, control proceeds to step ST53 where the program determines whether the fetal biparietal diameter (BPD) was measured at the last ultrasound. If the fetal biparietal diameter (BPD) was measured at the last ultrasound, the program proceeds to step ST54 and determines whether the patient's weight at 182 days and rate of weight gain during third trimester are known. If both are known, the program uses Equation 19 to predict birth weight (step ST55). If only the patient's weight at 182 days is known, the program uses Equation 20 to predict birth weight (step ST56). If only the rate of weight gain during the third trimester is known, the program uses Equation 21 to predict birth weight (step ST57). If neither parameter is known, the program uses Equation 22 to predict birth weight (step ST58).

Returning to step ST53, if the fetal biparietal diameter (BPD) was not measured at the last ultrasound, control proceeds to step ST59 where the program determines whether the patient's weight at 182 days and rate of weight gain during the third trimester are known. If both parameters are known, the program uses Equation 23 to predict birth weight (ST60). If only the patient's weight at 182 days is known, the program uses Equation 24 to predict birth weight (step ST61). If only the rate of weight gain during the third trimester is known, the program uses Equation 25 to predict birth weight (ST62). Finally, if neither rate of weight gain during the third trimester nor the patient's weight at 182 days is known, the program uses Equation 26 to predict birth weight (ST63).

Figure 3E:
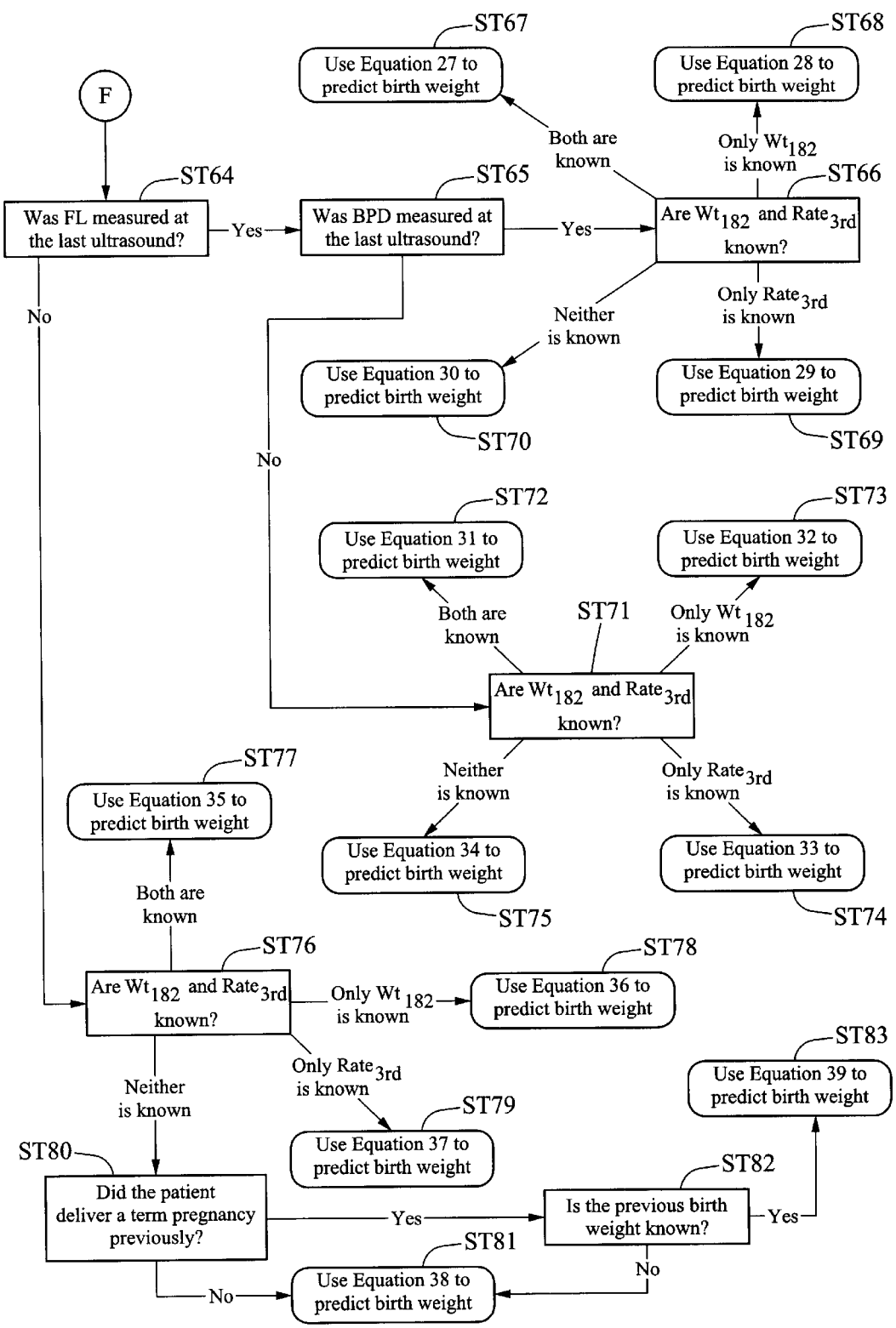

FIG. 3E illustrates exemplary steps that may be performed by fetal birth weight/macrosomia risk estimation software 110 in estimating birth weight if the fetal head circumference (HC) was not measured at the last ultrasound. Entry is via connector F from the preceding flow chart 3D at ST46. Referring to FIG. 3E, in step ST64, the program determines whether the fetal femur length (FL) was measured at the last ultrasound. If femur length was measured at the ultrasound, control proceeds to step ST65 where the program determines whether the fetal biparietal diameter (BPD) was measured at the last ultrasound. If the fetal biparietal diameter (BPD) was measured at the last ultrasound, control proceeds to step ST66 where the program determines whether the patient's weight at 182 days and rate of weight gained during the third trimester are known. If both parameters are known, the program uses Equation 27 to predict birth weight (step ST67). If only the patient's weight at 182 days is known, the program uses Equation 28 to predict birth weight (step ST68). If only the rate of weight gain during the third trimester is known, the program uses Equation 29 to predict birth weight (step ST69). If neither parameter is known, the program uses Equation 30 to predict birth weight (step ST70).

Returning to step ST65, if the fetal biparietal diameter (BPD) was measured at the last ultrasound, control proceeds to step ST71 where the program determines whether the patient's weight at 182 days and rate of weight gain during third trimester are known. If both are known, the program uses Equation 31 to predict birth weight (step ST72). If only the patient's weight at 182 days is known, the program uses Equation 32 to predict birth weight (step ST73). If only the rate of weight gain during the third trimester is known, the program uses Equation 33 to predict birth weight (step ST74). If neither parameter is known, the program uses Equation 34 to predict birth weight (step ST75).

Returning to step ST64, if the fetal femur length (FL) was measured at the last ultrasound, control proceeds to step ST76 where the program determines whether the patient's weight at 182 days and rate of weight gain during the third trimester are known. If both parameters are known, the program uses Equation 35 to predict birth weight (step ST77). If only the patient's weight at 182 days is known, the program uses Equation 36 to predict birth weight (step ST78). If only the rate of weight gain during the third trimester is known, the program uses Equation 37 to predict birth weight (step ST79).

If neither parameter is known, control proceeds to step ST80 where the program determines whether the patient has delivered a term pregnancy previously. If the patient has not delivered a term pregnancy previously, the program uses Equation 38 to predict birth weight (step ST81). If the patient has delivered a term pregnancy previously, in step ST82, the program determines whether the previous birth weight is known. If the previous birth weight is not known, the program uses Equation 38 to predict birth weight (step ST81). If the previous birth weight is known, the program uses Equation 39 to predict birth weight (step ST83).

Figure 3F:
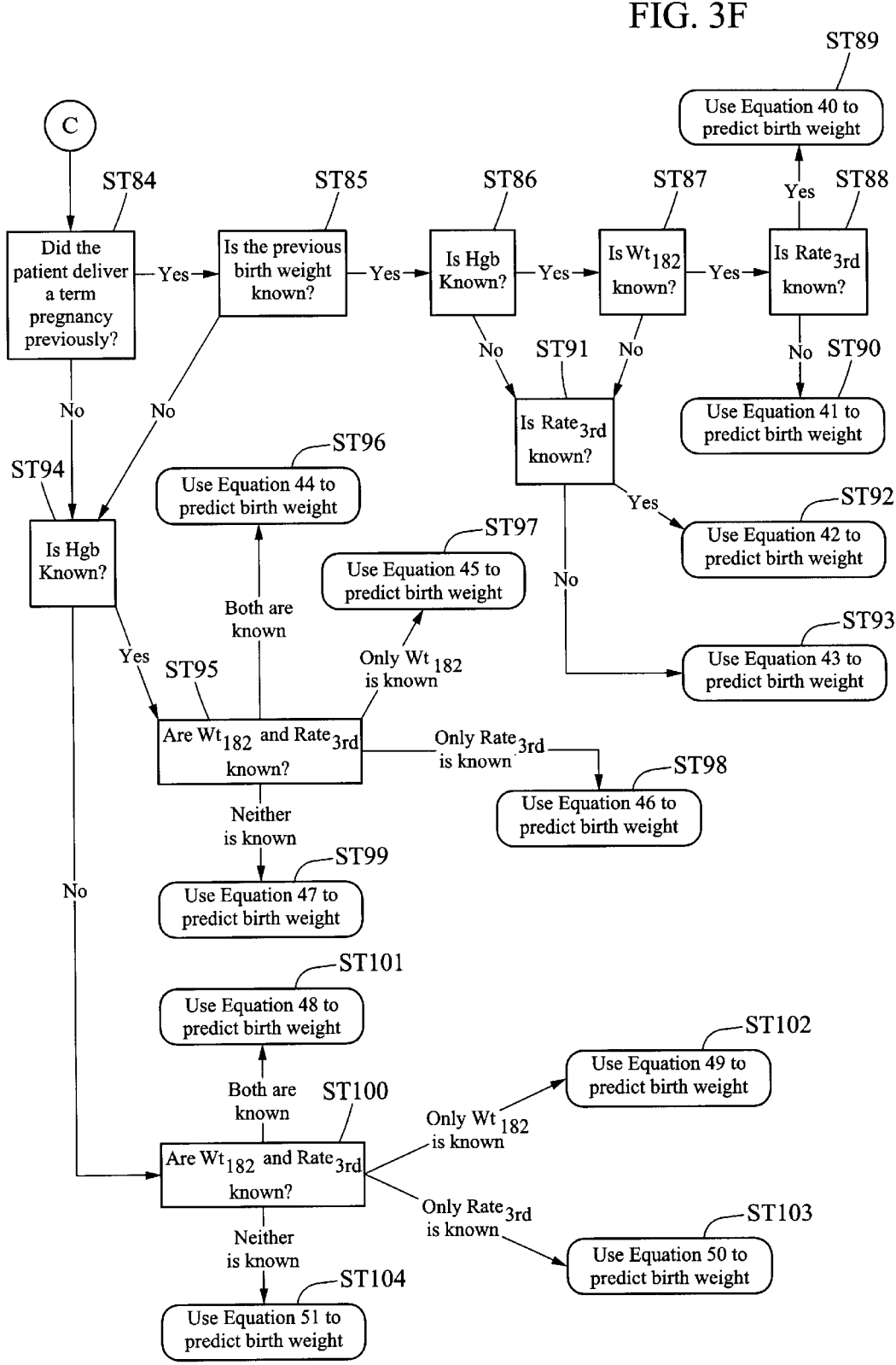

FIG. 3F illustrates exemplary steps that may be performed by fetal birth weight/macrosomia risk estimation software 110 for Caucasian patients. Entry is via connector C from the previous flow sheet 3B in ST22. Referring to FIG. 3F, in step ST84 the program determines whether the patient has delivered a term pregnancy previously. If the program determines that the patient has delivered a term pregnancy previously, control proceeds to step ST85 where the program determines whether the previous birth weight is known. If the previous birth weight is known, control proceeds to step ST86 where the program determines whether the patient's third trimester venous hemoglobin concentration is known. If the patient's third trimester venous hemoglobin concentration is known, control proceeds to step ST87 where the program determines whether the patient's weight at 182 days is known. If the program determines that the patient's weight at 182 days is known, control proceeds to step ST88 where the program determines whether the patient's rate of weight gain during the third trimester is known. If the rate of weight gain during the third trimester is known, the program uses Equation 40 to predict birth weight (step ST89). If, at step ST88, the rate of weight gain during the third trimester is not known, the program uses Equation 41 to predict birth weight (step ST90).

In steps ST86 or ST87, if the hemoglobin measurement or weight at 182 days is not known, control proceeds to step ST91 where the program determines whether the patient's rate of weight gain during the third trimester is known. If the patient's rate of weight gain during the third trimester is known, the program uses Equation 42 to predict birth weight (step ST92). If the patient's rate of weight gain during the third trimester is not known, the program uses Equation 43 to predict birth weight (step ST93).

In steps ST84 and step ST85, if the program determines that the patient did not deliver a term pregnancy previously or that the previous birth weight was not known, control proceeds to step ST94 where the program determines whether the patient's venous hemoglobin concentration during the third trimester is known. If the patient's hemoglobin concentration is known, control proceeds to step ST95 where the program determines whether the patient's weight at 182 days and the rate of weight gain during the third trimester are known. If both parameters are known, program uses Equation 44 to predict birth weight (step ST96). If only weight at 182 days is known, the program uses Equation 45 to predict birth weight (step ST97). If only the rate of weight gain during the third trimester is known, the program uses Equation 46 to predict birth weight (step ST98). If neither parameter is known, the program uses Equation 47 to predict birth weight (step ST99).

Returning to step ST94, if the program determines that the venous hemoglobin concentration during the third trimester is not known, control proceeds to step ST100 where the program determines whether the patient's weight at 182 days and rate of weight gain during the third trimester are known. If both parameters are known, the program uses Equation 48 to predict birth weight (step ST101). If only the patient's weight at 182 days is known, the program uses Equation 49 to predict birth weight (step ST102). If only the rate of weight gain during the third trimester is known, the program uses Equation 50 to predict birth weight (step ST103). If neither parameter is known, the program uses Equation 51 to predict birth weight (step ST104).

Figure 3G:
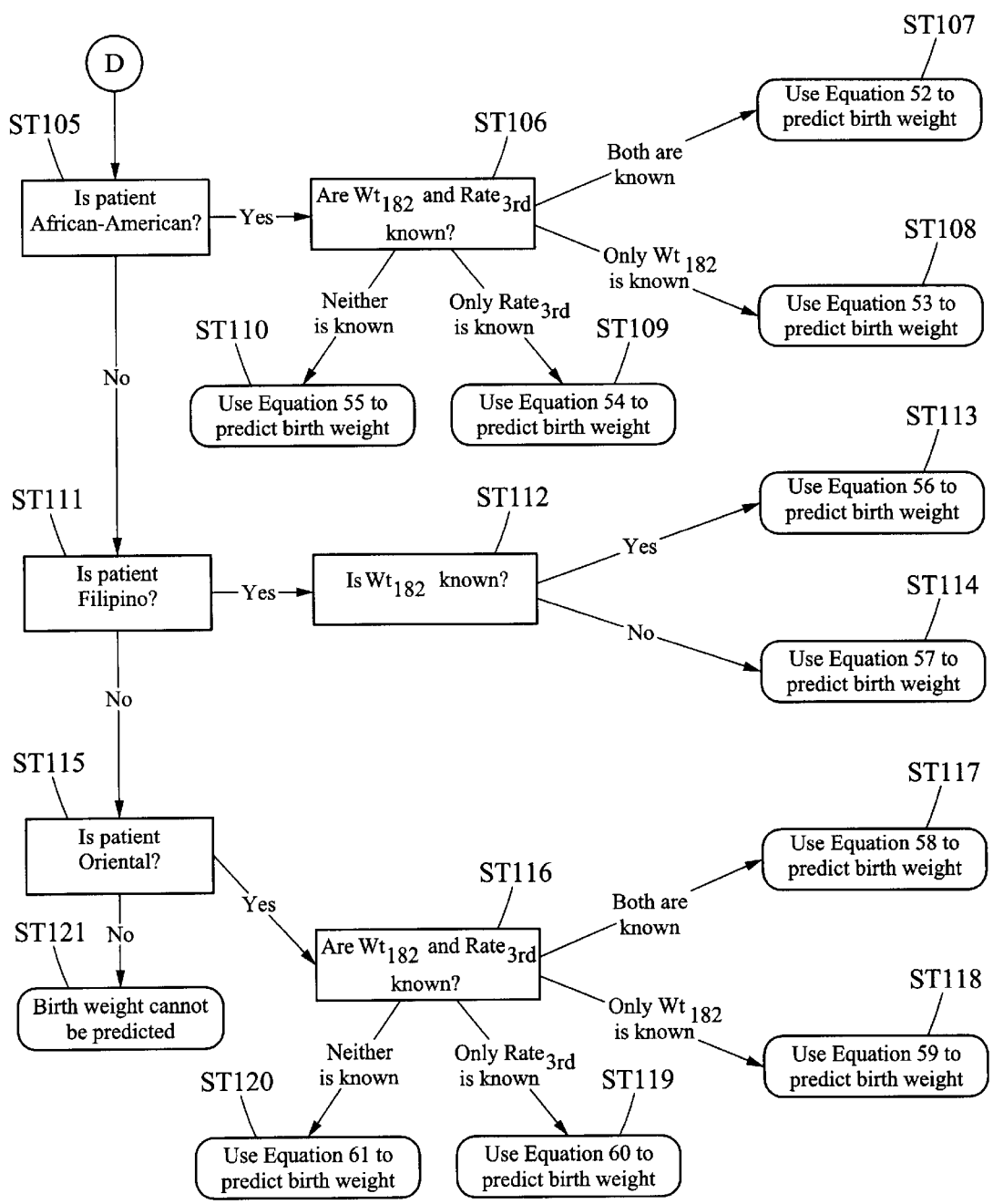

FIG. 3G is a flow chart illustrating exemplary steps performed by fetal birth weight/macrosomia risk estimation software 110 in estimating fetal birth weight for non-Caucasian patients. Entry is via connector D from previous flow chart 3B at ST22. Referring to FIG. 3G, in step (ST105), the program determines whether the patient is African-American. If the program determines that the patient is African-American, control proceeds to step ST106 where the program determines whether the patient's weight at 182 days and rate of weight gain during the third trimester are known. If both parameters are known, the program uses Equation 52 to predict birth weight (step ST107). If only the patient's weight at 182 days is known, the program uses Equation 53 to predict birth weight (step ST108). If only the rate of weight gain during the third trimester is known, the program uses Equation 54 to predict birth weight (step ST109). If neither parameter is known, the program uses Equation 55 to predict birth weight (ST110).

If the program determines in step ST105 that the patient is not African-American, control proceeds to step ST111 where the program determines whether the patient is Filipino. If the program determines that the patient is Filipino, control proceeds to step ST112 where the program determines whether the patient's weight at 182 days is known. If the patient's weight at 182 days is known, the program uses Equation 56 to predict birth weight (step ST113). If the patient's weight at 182 days is not known, the program uses Equation 57 to predict birth weight (step ST114).

In step ST111, if the program determines that the patient is not Filipino, control proceeds to step ST115 where the program determines whether the patient is Oriental. If the patient is Oriental, control proceeds to step ST116 where the program determines whether the patient's weight at 182 days and rate of weight gain during the third trimester are known. If the program determines that both parameters are known, the program uses Equation 58 to predict birth weight (step ST117). If the program determines that only the patient's weight at 182 days is known, the program uses Equation 59 to predict birth weight (step ST118). If the program determines that only rate of weight gain during the third trimester is known, the program uses Equation 60 to predict birth weight (step ST119). If the program determines that neither parameter is known, the program uses Equation 61 to predict birth weight (step ST120). Finally, in step ST115, if the program determines that the patient is not Oriental, the program may output a message indicating that birth weight cannot be predicted.

Thus, as illustrated in FIGS. 3A through 3G, fetal birth weight/macrosomia risk estimation software 110 estimates birth weight based on known information and uses the known information to select an optimal and uniquely developed equation in a predetermined hierarchy of equations that will allow the output of the most reliable fetal birth weight estimate that is possible given the type of information that is known and available.

In addition to calculating and outputting the predicted birth weight, fetal birth weight/macrosomia risk estimation software 110 may also output confidence intervals associated with each birth weight prediction. These confidence intervals have been determined empirically for each equation. Table 1 shown below illustrates the currently available and exemplary 80% confidence intervals for the equations listed above for estimating fetal birth weight. Using Table 1, 10 percent of actual birth weights can be expected to be below the individually predicted birth weight for each fetus minus the numerical cell entry for each equation, and 10% can be expected to be above the individually predicted birth weight for each fetus plus the numerical cell entry for each equation. Thus, by adding the numerical cell entry for each equation to the individually predicted birth weight for each fetus, the actual birth weight of the fetus on the specified target date will fall at or below the summation value in 90 percent of cases.

TABLE 1

Confidence Intervals for
Individual Fetal Birth Weight Estimation Equations

| Equation | Mean 80% Confidence Interval (in grams) |
|---|---|
| Equation 1 | 427 |
| Equation 2 | 441 |
| Equation 3 | 422 |
| Equation 4 | 438 |
| Equation 5 | 431 |
| Equation 6 | 447 |
| Equation 7 | 435 |
| Equation 8 | 449 |
| Equation 9 | 448 |
| Equation 10 | 468 |
| Equation 11 | 440 |
| Equation 12 | 454 |
| Equation 13 | 442 |
| Equation 14 | 458 |
| Equation 15 | 471 |
| Equation 16 | 482 |
| Equation 17 | 479 |
| Equation 18 | 494 |
| Equation 19 | 477 |
| Equation 20 | 488 |
| Equation 21 | 485 |
| Equation 22 | 500 |
| Equation 23 | 483 |
| Equation 24 | 492 |
| Equation 25 | 491 |
| Equation 26 | 505 |
| Equation 27 | 494 |
| Equation 28 | 508 |
| Equation 29 | 496 |
| Equation 30 | 512 |
| Equation 31 | 537 |
| Equation 32 | 547 |
| Equation 33 | 539 |
| Equation 34 | 558 |
| Equation 35 | 509 |
| Equation 36 | 509 |
| Equation 37 | 522 |
| Equation 38 | 524 |
| Equation 39 | 567 |
| Equation 40 | 491 |
| Equation 41 | 507 |
| Equation 42 | 521 |
| Equation 43 | 538 |
| Equation 44 | 484 |
| Equation 45 | 495 |
| Equation 46 | 503 |
| Equation 47 | 516 |
| Equation 48 | 492 |
| Equation 49 | 495 |
| Equation 50 | 508 |
| Equation 51 | 523 |
| Equation 52 | 496 |
| Equation 53 | 506 |
| Equation 54 | 487 |
| Equation 55 | 513 |
| Equation 56 | 539 |
| Equation 57 | 541 |
| Equation 58 | 440 |
| Equation 59 | 451 |
| Equation 60 | 437 |
| Equation 61 | 463 |

Figure 4A:
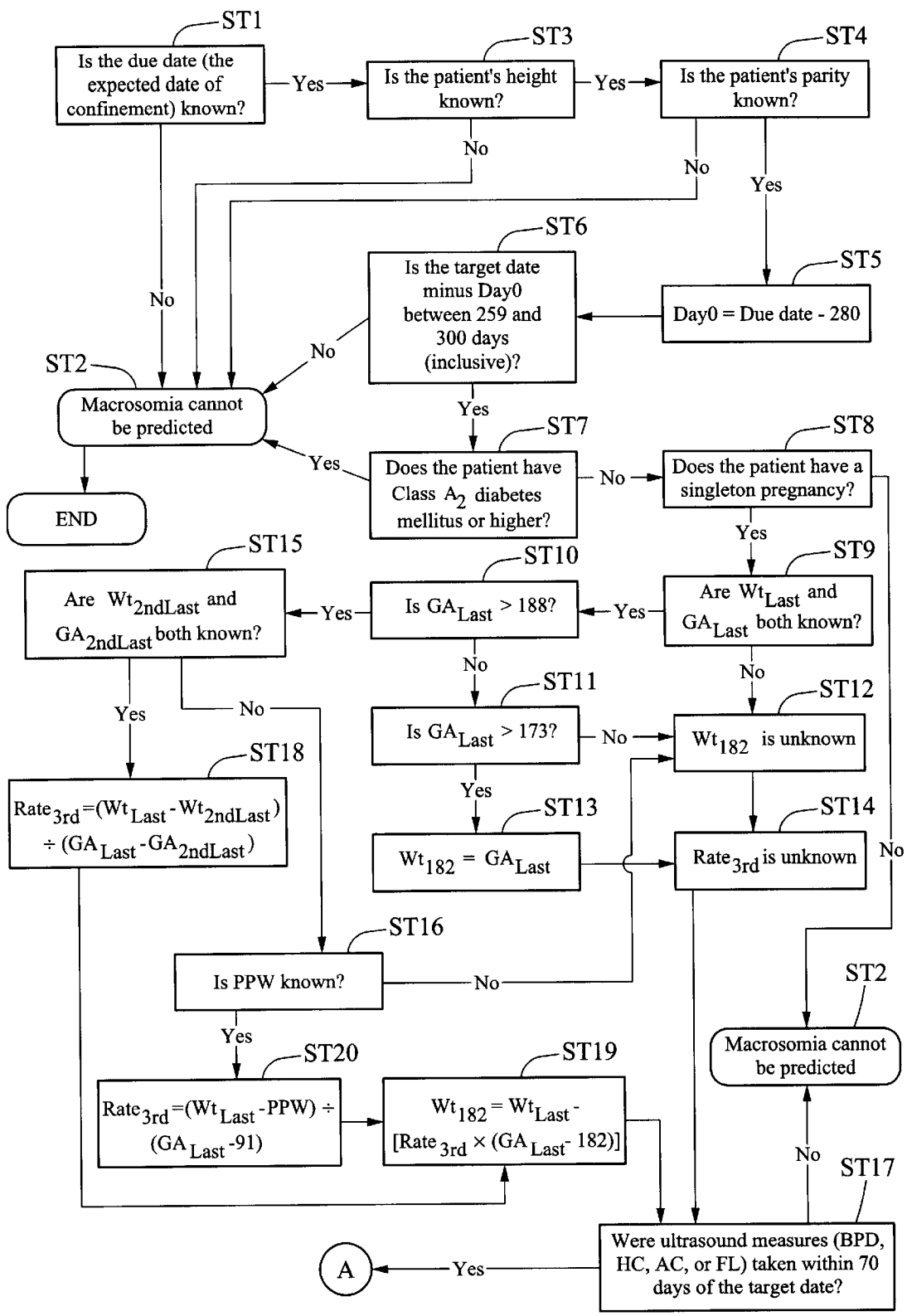
FIGS. 4A and 4B illustrate exemplary steps for estimating risk of fetal macrosomia according to an embodiment of the present invention.
Figure 4B:
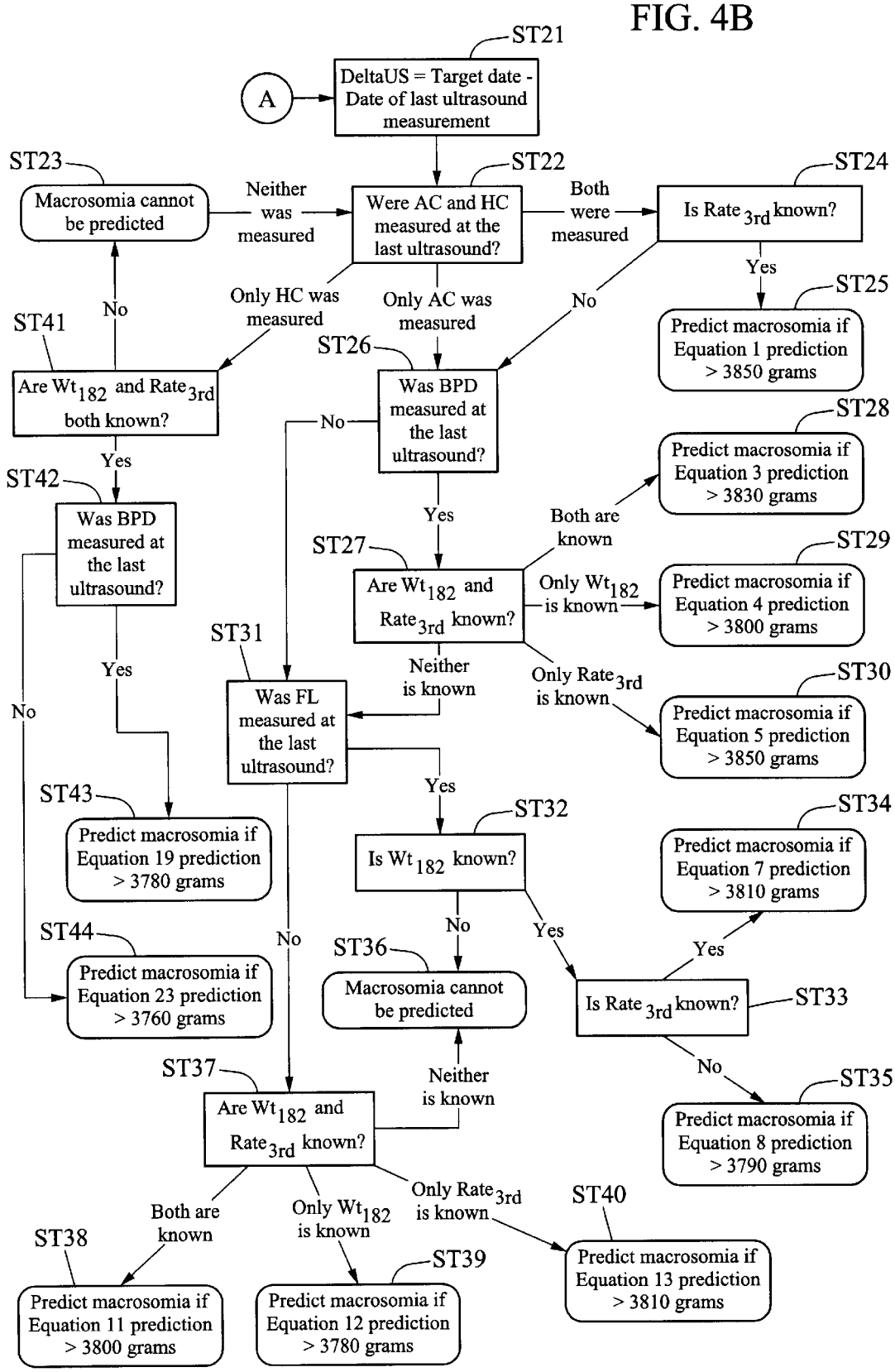

In addition to estimating fetal birth weight, fetal birth weight/macrosomia risk estimation software 110 may also calculate risk of macrosomia. FIGS. 4A and 4B illustrate exemplary steps that may be performed by fetal birth weight/macrosomia risk estimation software 110 in estimating risk of macrosomia. Referring to FIG. 4A, in step ST1, the program determines whether the expected due date is known. The expected due date may be estimated using any of the methods described above with regards to FIG. 3A. If the expected due date is not known, control proceeds to step ST2 where the program determines that risk of macrosomia cannot be predicted. After this step, processing for estimating risk of macrosomia ends.

If the expected due date is known, control proceeds to step ST3 where the program determines whether the patient's (i.e., the mother's) height is known. If the patient's height is not known, control proceeds to step ST2 where the program determines that risk of macrosomia cannot be predicted. If the patient's height is known, control proceeds to step ST4 where the program determines whether the patient's parity is known. As indicated above, the term parity refers to the number of prior children to which the patient has given birth. If the patient's parity is not known, control proceeds to step ST2, where the program determines that risk of macrosomia cannot be predicted.

If, on the other hand, the program determines that the patient's parity is known, control proceeds to step ST5 where the program calculates the value for a variable referred to herein as Day0 (defined above). In step ST6, the program calculates whether the target date minus Day0 is between 259 and 300 days inclusive. If the program determines that the target date minus Day0 is not between 259 and 300 days inclusive, control proceeds to step ST2 where the program determines that risk of macrosomia cannot be predicted.

If the program determines that the target date minus Day0 is between 259 and 300 days inclusive, control proceeds to step ST7 where the program determines whether the patient has Class $A_2$ insulin-dependent diabetes or higher. If the patient has Class $A_2$ insulin-dependent diabetes or higher, control proceeds to step ST2 where the program determines that risk of macrosomia cannot be predicted. If the program determines that the patient does not have Class $A_2$ insulin-dependent diabetes or higher, control proceeds to step ST8 where the program determines whether the patient has a singleton pregnancy. If the program determines that the patient does not have a singleton pregnancy, control proceeds to step ST2 where the program determines that risk of macrosomia cannot be predicted.

If the program determines that the patient has a singleton pregnancy, control proceeds to step ST9 where the program determines whether the patient's weight and the gestational age at the time of the last weight measurement are both known. If the last recorded weight of the patient and the gestational age at the time of the last recorded weight are not both known, control proceeds to step ST12, where the program determines that the patient's weight at 182 days is unknown, and to step ST14, where the program determines that the patient's third trimester weight gain rate is unknown. Control then proceeds to step ST17, where the program determines whether fetal ultrasound measurements were taken within 70 days of the target date. If fetal ultrasound measurements were taken within 70 days of the target date, control proceeds to the flow chart illustrated in FIG. 4B through connector A in FIG. 4A. Otherwise, control proceeds to step ST2, where the program determines that risk of macrosomia cannot be predicted If in step ST9, the program determines that the last recorded weight of the patient and the gestational age at the time of the last recorded weight are both known, control proceeds to step ST10 where it is determined whether the gestational age on which the patient's weight was last measured is greater than 188 days. If the gestational age is not greater than 188 days control proceeds to step ST11 where the program determines whether the gestational age on which the patient's weight was last measured is greater than 173 days. If the age is not greater than 173 days control proceeds to step ST12 where it is determined that the patient's weight 182 days after is not known.

If in step ST11, the program determines that the gestational age corresponding to the day on which the patient's weight was last measured is between 173 and 188 days, control proceeds to step ST13 where the program sets the patient's weight at 182 days to the patient's weight at the last weight measurement. Control then proceeds to step ST14 where the program determines that the rate of weight gain during the third trimester is unknown. If in step ST10, the program determines that the gestational age at the last ultrasound measurement is greater than 188 days, control proceeds to step ST15 where the program determines whether the second-to-last weight and second-to-last gestational age are both known. If neither parameter is known, control proceeds to step ST16 where the program determines whether the patient's pre-pregnancy weight is known. If the patient's pre-pregnancy weight is not known, control proceeds to steps ST12 and ST14 where the program determines that the patient's weight at 182 days is not known and that the patient's rate of weight gain during the third trimester is not known. If the rate of weight gain during the third trimester and the patient's weight at 182 days are both unknown, control proceeds to step ST17 where the program determines whether fetal ultrasound measurements were taken within 70 days of the target date. If fetal ultrasound measurements were taken within 70 days of the target date, control proceeds to the flow chart illustrated in FIG. 4B through connector A in FIG. 4A. Otherwise, if no fetal ultrasound measurements were taken within 70 days of the target date, control proceeds to step ST2, where the program determines that risk of macrosomia cannot be predicted.

Returning to step ST15 in FIG. 4A, if the patient's weight second-to-last measurement and the corresponding gestational age are both known, control proceeds to step ST18, where the program calculates the rate of weight gain during the third trimester. Control then proceeds to step ST19 where the program uses the rate calculated in step ST18 to calculate the patient's weight at 182 days. Control then proceeds to step ST17 where the program determines whether fetal ultrasound measurements were taken within seventy days of the target date. Similarly, in step ST16, if the pre-pregnancy weight is known, in step ST20, the rate of weight gain during the third trimester is calculated using the pre-pregnancy weight and control proceeds to step ST19 where the patient's weight at 182 days is calculated. Control then proceeds to step ST17 where the program determines whether fetal ultrasound measurements were taken within seventy days of the target date.

Once the program either calculates the patient's weight at 182 days or determines that the patient's weight at 182 days is not known, control proceeds to the flow chart illustrated in FIG. 4B through connecter A. Referring to FIG. 4B, in step ST21, the program computes a quantity DeltaUS, which indicates the number of days elapsed between the time of ultrasonographic fetal measurements and the target date. In step ST22, the program determines whether the fetal abdominal circumference (AC) and head circumference (HC) were measured at the last ultrasound. If neither was measured, in step ST23, the program determines that risk of macrosomia cannot be predicted. If both were measured, control proceeds to step ST24 where the program determines whether the rate of weight gain during the third trimester is known. If the rate of weight gain during the third trimester is known, the program uses Equation 1 listed above to predict risk of macrosomia (step ST25). More particularly, if Equation 1 indicates that the predicted birth weight is greater than a predetermined value, macrosomia is predicted. In one example, the predetermined value for Equation 1 may be about 3850 grams. However, the present invention is not limited to using 3850 grams as the value for indicating macrosomia. Any suitable value for predicting risk of macrosomia is intended to be within the scope of the invention. In addition, as indicated in FIG. 4B, the predetermined value used to indicate macrosomia may vary with the equation used.

Returning to step ST24, if the program determines that the rate of weight gain during the third trimester is not known, control proceeds to step ST26 where the program determines whether biparietal diameter was measured at the last ultrasound. If the program determines that biparietal diameter was measured at the last ultrasound, control proceed to step ST27 where the program determines whether the patient's weight at 182 days and the rate of weight gain during the third trimester are known. If both parameters are known, in step ST28, the program uses Equation 3 to predict risk of macrosomia. More particularly, if Equation 3 indicated that the predicted birth weight is greater than a predetermined value, such as 3850 grams, macrosomia is predicted.

Returning to step ST27, if only the patient's weight at 182 days is known, the program uses Equation 4 to predict risk of macrosomia (step ST29). Again, an exemplary prediction threshold value for Equation 4 of >3,800 grams is shown as an example of a cutoff for predicting macrosomia, but the scope of this invention is not intended to be limited to a particularly chosen predetermined cutoff value. If only the rate of gain during the third trimester is known, the program uses Equation 5 to predict macrosomia, using an exemplary cutoff value of >3,850 grams for predicting fetal macrosomia (step ST30). If neither parameter is known, control proceeds to step ST31 where the program determines whether the fetal femur length (FL) was measured at the last ultrasound. If the fetal femur length (FL) was measured at the last ultrasound, control proceeds to steps ST32 and ST33 where the program determines whether maternal weight at 182 days and rate of weight gain during the third trimester are known. If both are known, in step ST34, the program uses Equation 7 to predict macrosomia, using an exemplary fetal weight threshold value of >3,810 grams. If only the patient's weight at 182 days is known, program uses Equation 8 to predict macrosomia, using an exemplary threshold value of >3,790 grams (step ST35). Returning to step ST32, if the maternal weight at 182 days is not known, control proceeds to step ST36, where the program determines that risk of macrosomia cannot be predicted.

Returning again to step ST31, if femur length was not measured at the last ultrasound, control proceeds to step ST37 where the program determines whether the patient's weight at 182 days and rate of weight gain during the third trimester are known. If both are known, in step ST38, the program uses Equation 11 to predict macrosomia, using an exemplary threshold value of >3,800 grams. If only the patient's weight at 182 days is known, the program uses Equation 12 to predict macrosomia, using an exemplary threshold value of >3,780 grams (step ST39). If only the rate of weight gain during the third trimester is known, the program uses Equation 13 to predict macrosomia, using an exemplary threshold value of >3,810 grams (step ST40). Finally, if neither is known, the program determines that risk of macrosomia cannot be predicted.

Returning to step ST22, if the program determines that only the fetal head circumference (HC) was measured in the last ultrasound, control proceeds to step ST41 where the program determines whether the patient's weight at 182 days and rate of weight gain during the third trimester are known. If either or both of these parameters are unknown, control proceeds to step ST23 where the program determines that macrosomia cannot be predicted. If both parameters are known, control proceeds to step ST42 where the program determines whether the fetal biparietal diameter (BPD) was measured at the last ultrasound. If the fetal biparietal diameter (BPD) was measured at the last ultrasound, control proceeds to step ST43 where the program predicts macrosomia using Equation 19, using an exemplary threshold value of >3,780 grams. If the fetal biparietal diameter (BPD) was not measured at the last ultrasound, control proceeds to step ST44 where the program predicts macrosomia using Equation 23, using an exemplary threshold value of >3,760 grams.

Thus, as illustrated in FIGS. 4A and 4B, fetal birth weight/risk of macrosomia estimation software 110 can predict risk of macrosomia using a subset of the equations used to predict fetal birth weight. Predicting whether or not macrosomia will occur is useful in reducing health risks to both the mother and the unborn child.

In addition to producing binary output indicating whether or not macrosomia is suspected to exist on the specified target date, fetal birth weight/macrosomia risk estimation software 110 may also calculate and output percentages indicating the risk of macrosomia at birth. The following equations and the table that follows may be used by fetal birth weight/macrosomia risk estimation software 110 in predicting the risk of fetal macrosomia on the target date as a percentage in each case, depending upon which equation in the hierarchy of equations is used to calculate the risk of fetal macrosomia.

Probability of macrosomia (in %), given a predicted birth weight=(BaseProb×$P_{macro}$)÷[(100−BaseProb)× $P_{Nonmac}$+BaseProb×$P_{Macro}$], where $P_{macro}$=Probability that a macrosomic delivery will have the predicted birth weight=exp{−0.5×[(Pred−$M_{Macro}$) ÷$SD_{Macro}$]$^2$}÷[$SD_{Macro}$×sqrt(2π)]

$P_{nonmac}$=Probability that a non-macrosomic delivery will have the predicted birth weight=exp{−0.5×[(Pred− $M_{Nonmac}$)÷$SD_{Nonmac}$]$^2$}÷[$SD_{Nonmac}$×sqrt(2π)]

Pred=The predicted birth weight, in grams $M_{Macro}$=The mean predicted birth weight for macrosomic deliveries, in grams $M_{Nonmac}$=The mean predicted birth weight for non-macrosomic deliveries, in grams $SD_{Macro}$=The standard deviation of the predicted birth weight for macrosomic deliveries, in grams $SD_{Nonmac}$=The standard deviation of the predicted birth weight for non-macrosomic deliveries, in grams and BaseProb=Base rate of macrosomia (in %) =13% for Caucasians, 8% for African Americans, 7% for Filipinos, and 6% for Orientals Values for $M_{Macro}$, $SD_{Macro}$, $M_{Nonmac}$, and $SD_{Nonmac}$ vary with the prediction equation that is used to predict fetal macrosomia. These values, as presently known from empirical data, are indicated for each equation in Table 2 below.

TABLE 2

Macrosomia Risk Equation Variable Values

| Equation | $M_{Macro}$ | $SD_{Macro}$ | $M_{Nonmac}$ | $SD_{Nonmac}$ |
|---|---|---|---|---|
| 1 | 3884 | 198 | 3403 | 356 |
| 3 | 3891 | 201 | 3389 | 344 |
| 4 | 3853 | 218 | 3394 | 336 |
| 5 | 3881 | 197 | 3401 | 349 |
| 7 | 3864 | 219 | 3387 | 338 |
| 8 | 3828 | 238 | 3392 | 330 |
| 11 | 3863 | 239 | 3385 | 330 |
| 12 | 3828 | 252 | 3390 | 324 |
| 13 | 3851 | 232 | 3385 | 324 |
| 19 | 3804 | 241 | 3410 | 307 |
| 23 | 3794 | 236 | 3409 | 303 |

In Table 2, the stated values for the macrosomia risk equation variables are preferred values that have been obtained through empirical observation and experimentation. However, the present invention is not limited to using these exact values. Any suitable coefficients for obtaining accurate macrosomia risk predictions are intended to be within the scope of the invention.

Table 3 shown below illustrates the risks associated with macrosomia.

TABLE 3

Risks Associated with Macrosomia
Newborn and Maternal Complications Associated with Delivery of Fetuses Weighing >4,000 grams*

| | Birth Weight >4,000 gm | |
|---|---|---|
| Complication | Relative Risk[a] | Absolute Risk (%) |
| Shoulder Dystocia | 2.0–38 | 2–18% |
| Brachial Palsy | 16–216 | 0.2–8% |
| Bony Injuries/Fracture | 1.4–97 | 0.2–7% |
| Prolonged Labor | 2.2–3.2 | 4–19% |
| Birth Asphyxia/Low Apgar Scores | 1.7–5.6 | 1–14% |
| Forceps/Vacuum Extraction | 1.5–3.6 | 11–39% |
| Birth Canal/Perineal Lacerations | 1.6–5.1 | 3–11% |
| Postpartum Hemorrhage | 1.6–5.2 | 4–6% |
| Cephalopelvic Disproportion | 1.9–2.2 | 8–9% |
| Cesarean Section | 1.2–2.9 | 13–39% |

*Data are compiled from 15 prior studies that have investigated both the relative risk and absolute risk of complications associated with the births of macrosomic fetuses. The ranges reflect differences among studies in the patient populations investigated as well as differences in the criteria used for the diagnosis of each complication.
[a]Relative risks are for fetuses weighing >4,000 grams at delivery versus controls having birth weights of ≤4,000 grams; the p-value associated with each relative risk is <.001 in all cases, except for Birth Canal/Perineal Lacerations, where the p-value is <.05.

All of the complications illustrated in Table 3 can be mitigated using the methods and systems for predicting fetal birth weight and risk of macrosomia described herein. For example, if fetal weight at birth and/or risk of macrosomia can be accurately predicted, preventative measures can be implemented that reduce the risk of harm to the child and to the mother. Since this invention permits the prediction of fetal weight at birth and the risk of fetal macrosomia as an ongoing function of gestational age, and since fetal weight increases universally with advancing gestational age, this invention permits the option to inform obstetrical practitioners when they may intervene and effect delivery in advance of the fetus's weight exceeding the high-risk threshold of 4,000 grams, as well as when the risk of fetal macrosomia at a particular target delivery date exceeds any specified and/or predetermined unacceptable risk percentage. Thus, the present invention is a significant advance in the field of pre-natal and intrapartum care.

Although the present invention has been described above with regard to steps performed by a computer program, the present invention is not limited to predicting birth weight or risk of macrosomia using a computer program. The equations and steps listed above can be performed manually without departing from the scope of the invention.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A method for estimating fetal weight at birth, the method comprising:
   (a) requesting information concerning maternal physical characteristics for a fetus for which birth weight is to be estimated;
   (b) requesting information concerning maternal medical conditions for a fetus for which birth weight is to be estimated;
   (c) requesting information concerning maternal laboratory results using maternal blood for a fetus for which birth weight is to be estimated;
   (d) requesting information concerning at least one ultrasonographically measured physical dimension of the fetus for which birth weight is to be estimated; and
   (e) estimating birth weight of the fetus based on the information obtained from steps (a)–(d), wherein estimating birth weight includes selecting, from a plurality of multivariable birth weight estimation equations for estimating birth weight as a function of gestational age for a particular individual, the most accurate equation for which birth weight can be calculated using available information obtained in steps (a)–(d), and calculating the birth weight using the selected equation.

2. The method of claim 1 wherein requesting information concerning maternal physical characteristics, maternal medical conditions, maternal laboratory results, and the information concerning at least one ultrasonographically measured physical dimensions of the fetus includes presenting a user with a questionnaire requesting the information.

3. The method of claim 2 wherein presenting a user with a questionnaire includes serving the questionnaire from a server to a client over a computer network.

4. The method of claim 2 wherein presenting the user with a questionnaire includes presenting the user with a questionnaire on a handheld computer.

5. The method of claim 2 wherein presenting the user with a questionnaire includes presenting the user with a questionnaire on a personal computer.

6. The method of claim 2 wherein presenting the user with a questionnaire includes presenting a user with software for execution on a computer associated with an ultrasound device.

7. The method of claim 2 wherein presenting the user with a questionnaire includes presenting the user with a questionnaire over the Internet.

8. The method of claim 1 wherein requesting information concerning maternal characteristics includes requesting information regarding maternal race, expected due date, and maternal illnesses, in addition to at least one of pre-pregnancy maternal weight, maternal weight during pregnancy, prior pregnancies, hemoglobin concentration, glucose screening test result, and altitude.

9. The method of claim 1 wherein requesting information concerning at least one ultrasonographically measured physical dimension includes requesting information concerning at least one of fetal abdominal circumference, fetal head circumference, fetal biparietal diameter, fetal femur length, and fetal sex.

10. The method of claim 1 wherein requesting information concerning at least one ultrasonographically measured physical dimension includes determining the presence or absence of information concerning at least one ultrasonographically measured physical dimension and wherein estimating birth weight includes, in response to determining the absence of at least one ultrasonographically measured physical dimension, estimating birth weight based on maternal characteristics only.

11. The method of claim 1 wherein steps (a)–(d) are performed manually.

12. The method of claim 1 comprising requesting information regarding paternal characteristics and wherein estimating birth weight of the fetus includes estimating birth weight based on information obtained regarding paternal characteristics in addition to the information concerning maternal and at least one ultrasonographically measured physical dimension.

13. The method of claim 1 comprising outputting a number on a computer display device, the number being the fetal birth weight estimate.

14. The method of claim 1 comprising outputting a range of birth weights with an associated degree of confidence.

15. The method of claim 1 comprising outputting an array of birth weights corresponding to an array of potential target dates of delivery.

16. The method of claim 1 comprising outputting an array of ranges of birth weights associated with a specified degree of confidence for an array of potential target dates of delivery.

17. The method of claim 1 comprising outputting a confidence interval associated with the selected multivariable birth weight estimation equation, the confidence interval indicating a range of birth weights into which the calculated birth weight is expected to fall and a probability associated with that range.

18. The method of claim 1 wherein the equations are adapted to estimate birth weight at a gestational age that is remote from a predicted delivery date.

19. A method for predicting risk of fetal macrosomia, the method comprising:
(a) requesting information concerning maternal physical characteristics for a fetus for which risk of macrosomia is to be estimated;
(b) requesting information concerning maternal medical conditions for a fetus for which risk of macrosomia is to be estimated;
(c) requesting information concerning maternal laboratory results using maternal blood for a fetus for which risk of macrosomia is to be estimated;
(d) requesting information concerning at least one ultrasonographically measured physical dimension of the fetus for which risk of macrosomia is to be estimated; and
(e) estimating the risk of macrosomia for the fetus based on information obtained in response to steps (a)–(d), wherein estimating the risk of macrosomia includes selecting, from a plurality of multivariable birth weight estimation equations for calculating birth weight as a function of gestational age for a particular individual, the most accurate equation for which birth weight can be calculated using available information obtained in response to (a)–(d), and calculating the risk of macrosomia based on the estimated birth weight using the selected equation.

20. The method of claim 19 wherein requesting information concerning maternal physical characteristics, maternal medical conditions, maternal laboratory results, and the information concerning at least one ultrasonographically measured physical dimension of the fetus includes presenting a user with a questionnaire requesting the information.

21. The method of claim 20 wherein presenting a user with a questionnaire includes serving the questionnaire from a server to a client over a computer network.

22. The method of claim 20, wherein presenting the user with a questionnaire includes presenting the user with a questionnaire on a handheld computer.

23. The method of claim 20 wherein presenting the user with a questionnaire includes presenting the user with a questionnaire on a personal computer.

24. The method of claim 20 wherein presenting the user with a questionnaire includes presenting a user with software for execution on a computer associated with an ultrasound device.

25. The method of claim 20 wherein presenting the user with a questionnaire includes presenting a user with a user interface over the Internet.

26. The method of claim 20 wherein the equations are adapted to estimate birth weight at a gestational age that is remote from a predicted delivery date.

27. The method of claim 19 wherein requesting information concerning maternal characteristics includes requesting information regarding maternal race, expected due date, and maternal illnesses, in addition to at least one of pre-pregnancy maternal weight, maternal weight during pregnancy, prior pregnancies, hemoglobin concentration, glucose screening test result, and altitude.

28. The method of claim 19 wherein requesting information concerning at least one ultrasonographically measured physical dimension includes requesting information concerning at least one of fetal abdominal circumference, fetal head circumference, fetal biparietal diameter, fetal femur length, and fetal sex.

29. The method of claim 19 wherein requesting information concerning at least one ultrasonographically measured physical dimension includes determining the presence or absence of information concerning at least one ultrasonographically measured physical dimension wherein estimating fetal macrosomia includes, in response to determining the absence of at least one ultrasonographically measured physical dimension, estimating fetal macrosomia based on maternal characteristics only.

30. The method of claim 19 comprising performing steps (a)–(d) manually.

31. The method of claim 19 comprising obtaining information regarding paternal characteristics and wherein estimating risk of macrosomia of the fetus includes estimating risk of macrosomia based on the information regarding paternal characteristics in addition to the information concerning maternal and at least one ultrasonographically measured fetal physical dimension.

32. The method of claim 19 comprising outputting on a computer display device, an indicator of the risk of macrosomia.

33. The method of claim 32 wherein the indicator represents the presence or absence of macrosomia.

34. The method of claim 32 wherein the indicator represents a percentage risk of macrosomia.

35. The method of claim 19 comprising outputting a confidence interval associated with the selected multivariable birth weight estimation equation, the confidence interval indicating a range of birth weights into which the calculated birth weight is expected to fall and a probability associated with that range.

36. A computer program product comprising computer-executable instructions embodied in a computer-readable medium for performing steps comprising:
  (a) requesting information concerning maternal physical characteristics for a fetus;
  (b) requesting information concerning maternal medical conditions for a fetus;
  (c) requesting information concerning maternal laboratory results using maternal blood for the fetus;
  (d) obtaining information concerning at least one ultrasonographically measured physical dimension of the fetus; and
  (e) estimating at least one of birth weight, a range of birth weights, confidence intervals, and risk of macrosomia for the fetus based on information obtained in response to steps (a)–(d), wherein estimating birth weight, range of birth weights, confidence intervals and risk of macrosomia includes selecting, from a plurality of multivariate birth weight estimation equations for calculating birth weight for a particular individual as a function of gestational age, the most accurate equation for Which birth weight can be calculated using available information obtained in response to steps (a)–(d) and calculating the birth weight using the selected equation.

37. The computer program product of claim 36 wherein requesting information concerning maternal physical characteristics, maternal medical conditions, maternal laboratory results, and the information concerning ultrasonographically measured physical dimensions of the fetus includes presenting a user with a questionnaire requesting the information.

38. The computer program product of claim 37 wherein presenting a user with a questionnaire includes presenting the questionnaire from a server to a client over a computer network.

39. The computer program product of claim 37 wherein presenting the user with a questionnaire includes presenting the user with a questionnaire on a handheld computer.

40. The computer program product of claim 37 wherein presenting the user with a questionnaire includes presenting the user with a questionnaire on a personal computer.

41. The computer program product of claim 37 wherein presenting the user with a questionnaire includes presenting a user with software for execution on a computer associated with an ultrasound device.

42. The computer program product of claim 37 wherein presenting the user with a questionnaire includes presenting the user with a user interface over the Internet.

43. The computer program product of claim 36 wherein requesting information concerning maternal characteristics includes requesting information regarding maternal race, expected due date, and maternal illnesses, in addition to at least one of pre-pregnancy maternal weight, maternal weight during pregnancy, prior pregnancies, hemoglobin concentration, glucose screening test result, and altitude.

44. The computer program product of claim 36 wherein requesting information concerning at least one ultrasonographically measured physical dimension includes requesting information concerning least one of fetal abdominal circumference, fetal head circumference, fetal biparietal diameter, fetal femur length, and fetal sex.

45. The computer program product of claim 36 wherein requesting information concerning at least one ultrasonographically measured physical dimension includes determining the presence or absence of information concerning at least one ultrasonographically measured physical dimension and wherein estimating birth weight includes, in response to determining the absence of at least one ultrasonographically measured physical dimension, estimating birth weight based on maternal characteristics only.

46. The computer program product of claim 36 wherein estimating birth weight of a fetus includes estimating birth weight with an accuracy of at least about 8.5%.

47. The computer program product of claim 35 comprising requesting information regarding paternal characteristics and wherein estimating birth weight of the fetus includes estimating birth weight based on information obtained regarding paternal characteristics in addition to information obtained concerning maternal and at least one ultrasonographically measured physical dimension.

48. The computer program product of claim 35 comprising outputting a number on a computer display device, the number being the fetal birth weight estimate.

49. The computer program product claim 35 comprising outputting on a computer display device, an indicator of the risk of macrosomia.

50. The computer program product of claim 49 wherein the indicator represents the presence or absence of macrosomia.

51. The computer program product claim 49 wherein the indicator represents a percentage risk of macrosomia.

52. The computer program product of claim 36 comprising outputting a confidence interval associated with the selected multivariable birth weight estimation equation, the confidence interval indicating a range of birth weights into which the calculated birth weight is expected to fall and a probability associated with that range.

53. The computer program product of claim 36 wherein the equations are adapted to estimate birth weight at a gestational age that is remote from a predicted delivery date.

* * * * *

UNITED STATES PATENT AND TRADEMARK OFFICE
CERTIFICATE OF CORRECTION

PATENT NO. : 6,695,780 B1
DATED : February 24, 2004
INVENTOR(S) : Gerard Georges Nahum et al.

It is certified that error appears in the above-identified patent and that said Letters Patent is hereby corrected as shown below:

Column 8,
Line 53, replace "Equation 7: BWT=-2495+(11.87×AC)+(18.39×FL)+(18.79×DeltaUS)+(0.00008700×GAxHeight×Wt$_{182}$)+(3.260×GA×Rate3rd×[Parity+1])" with
-- Equation 7: BWT = -2495 + (11.87×AC) + (18.39×FL) + (18.79×DeltaUS) + (0.00008700 × GA × Height × Wt$_{182}$) + (3.260 × GA × Rate$_{3rd}$ × [Parity + 1]) --.

Column 22,
Line 47, replace "P$_{nonmac}$=Probability that a non-macrosomic delivery will have the predicted birth weight=exp{-0.5×[(Pred–M$_{Nonmac}$)+SD$_{Nonmac}$]$^2$}+[SD$_{Nonmac}$xsqrt(27π)]" with -- P$_{nonmac}$ =Probability that a non-macrosomic delivery will have the predicted birth weight = exp{-0.5 × [ (Pred – M$_{Nonmac}$) ÷ SD$_{Nonmac}$]$^2$ } ÷ [SD$_{Nonmac}$ × sqrt(2π) ] --.

Signed and Sealed this

Fifth Day of July, 2005

JON W. DUDAS
*Director of the United States Patent and Trademark Office*